(12) United States Patent
Matsuo

(10) Patent No.: US 9,854,984 B2
(45) Date of Patent: Jan. 2, 2018

(54) OPTICAL DETECTION UNIT AND BIOLOGICAL INFORMATION DETECTION DEVICE

(71) Applicant: Seiko Epson Corporation, Shinjuku-ku (JP)

(72) Inventor: Atsushi Matsuo, Tachikawa (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/991,057

(22) Filed: Jan. 8, 2016

(65) Prior Publication Data

US 2016/0120421 A1 May 5, 2016

Related U.S. Application Data

(63) Continuation of application No. PCT/JP2014/003646, filed on Jul. 9, 2014.

(30) Foreign Application Priority Data

Jul. 12, 2013 (JP) .................................. 2013-146239

(51) Int. Cl.
*A61B 5/1455* (2006.01)
*A61B 5/024* (2006.01)
(Continued)

(52) U.S. Cl.
CPC ...... *A61B 5/02427* (2013.01); *A61B 5/02055* (2013.01); *A61B 5/14552* (2013.01);
(Continued)

(58) Field of Classification Search
CPC ............ A61B 5/14552; A61B 5/02427; A61B 5/02416; A61B 5/681; A61B 2562/0233; A61B 2562/0238
See application file for complete search history.

(56) References Cited

U.S. PATENT DOCUMENTS 4,685,464 A 8/1987 Goldberger et al.
2008/0219673 A1 9/2008 Goh et al.
(Continued)

FOREIGN PATENT DOCUMENTS

JP 06-273229 A 9/1994
JP 6-42396 U 11/1994
(Continued)

OTHER PUBLICATIONS

Supplementary European Search Report dated Feb. 27, 2017 of the corresponding European Patent Application No. 14 822 176.5 (eight pages).

*Primary Examiner* — Tammie K Heller
(74) *Attorney, Agent, or Firm* — Kilpatrick Townsend & Stockton LLP

(57) ABSTRACT

An optical detection unit includes a light emitting portion 150 that emits light toward a target object, a light receiving portion 140 that receives light from the target object, and a light blocking member 70 that blocks light from being incident to at least the light receiving portion 140. The light blocking member 70 includes a light blocking wall 100 that is formed by performing sheet metal processing on a metal, and is provided between the light emitting portion 150 and the light receiving portion 140 so as to block light from the light emitting portion 150 from being incident to the light receiving portion 140. The light blocking wall 100 is formed of a first metal surface 71 of the light blocking member 70.

9 Claims, 13 Drawing Sheets

(51) Int. Cl.
    *A61B 5/0205*     (2006.01)
    *A61B 5/00*     (2006.01)

(52) U.S. Cl.
    CPC ............. *A61B 5/681* (2013.01); *A61B 5/721* (2013.01); *A61B 2562/0233* (2013.01); *A61B 2562/0238* (2013.01)

(56) References Cited

U.S. PATENT DOCUMENTS

| | | |
|---|---|---|
| 2010/0327164 A1 | 12/2010 | Costello et al. |
| 2011/0121181 A1* | 5/2011 | Costello ................ G01S 7/4813 250/338.1 |
| 2011/0166457 A1 | 7/2011 | Sato et al. |
| 2011/0260176 A1 | 10/2011 | Onoe et al. |
| 2012/0176599 A1* | 7/2012 | Leung .................... G01N 21/31 356/39 |
| 2013/0019459 A1 | 1/2013 | Lim et al. |
| 2013/0187891 A1 | 7/2013 | Eriksson et al. |
| 2014/0103199 A1* | 4/2014 | Loong ................... G01S 17/026 250/214.1 |
| 2016/0120421 A1 | 5/2016 | Matsuo |

FOREIGN PATENT DOCUMENTS

| | | |
|---|---|---|
| JP | 2004-061482 A | 2/2004 |
| JP | 2007-175415 A | 7/2007 |
| JP | 2009-168670 A | 7/2009 |
| JP | 2009-201919 A | 9/2009 |
| JP | 2010-200970 A | 9/2010 |
| JP | 2011-139725 A | 7/2011 |

\* cited by examiner

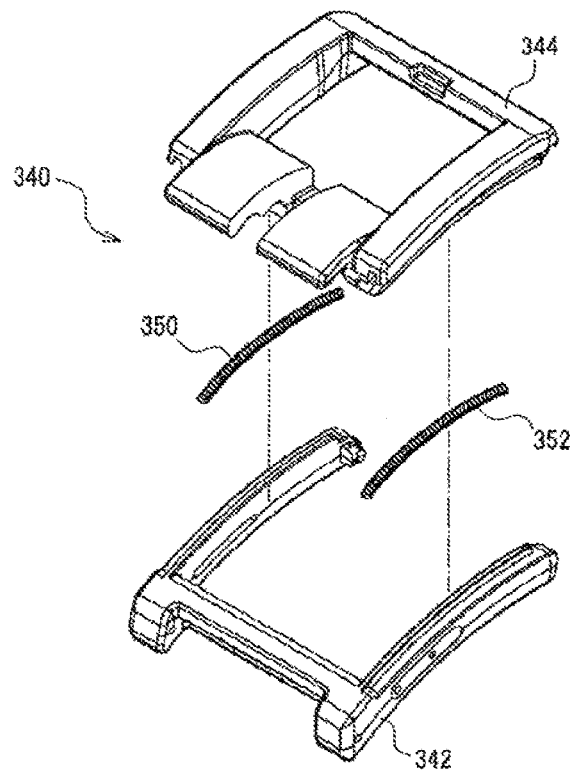
FIG. 7A
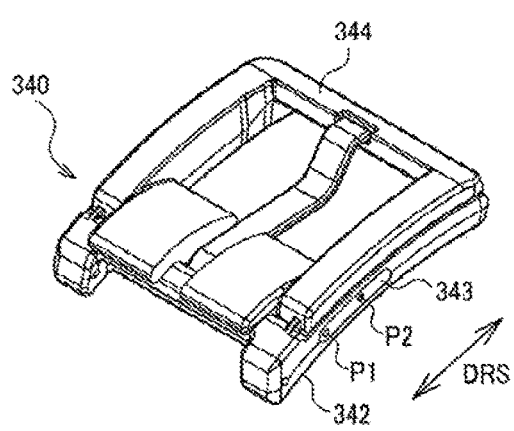
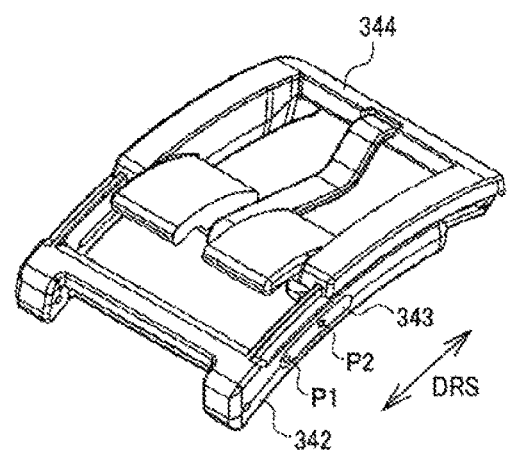
FIG. 7B　　　　　　　　FIG. 7C

OPTICAL DETECTION UNIT AND BIOLOGICAL INFORMATION DETECTION DEVICE

CROSS-REFERENCES TO RELATED APPLICATIONS

This application is a continuation of PCT Application No. PCT/JP2014/003646, filed Jul. 9, 2014, and Japanese Patent Application No. 2013-146239, filed Jul. 12, 2013, all the entireties of which are hereby incorporated by reference.

BACKGROUND

Technical Field

The present invention relates to an optical detection unit and a biological information detection device.

Background Art

In the related art, there is a biological information detection device which detects biological information such as a human pulse wave. PTLs 1 and 2 disclose the related art of a pulsimeter which is an example of such a biological information detection device. The pulsimeter is mounted on, for example, the arm, the wrist, or the finger, and detects pulsation derived from heartbeats of the human body so as to measure a pulse rate.

The pulsimeter disclosed in PTLs 1 and 2 is a photoelectric pulsimeter, and an optical detection unit thereof includes a light emitting portion which emits light toward a subject which is a target object, and a light receiving portion which receives light (light having biological information) from the subject. The pulsimeter detects a change in a blood flow rate as a change in an amount of received light so as to detect a pulse wave. In addition, PTL 1 discloses the pulsimeter of a type mounted on the wrist, and PTL 2 discloses the pulsimeter of a type mounted on the finger. Further, PTL 3 discloses an optical sensor in which a light blocking member is provided at a light receiving portion.

CITATION LIST

Patent Literature

PTL 1: JP-A-2011-139725
PTL 2: JP-A-2009-201919
PTL 3: JP-A-6-273229

SUMMARY OF INVENTION

Technical Problem

In such a detection device of biological information or the like, the light emitting portion of the optical detection unit emits light toward a target object, and various information pieces are detected on the basis of a detection signal which is obtained as a result of the light receiving portion receiving light from the target object. Therefore, it is important to improve quality of the detection signal. For example, if light from the light emitting portion is incident to the light receiving portion, there is a concern that reliability of detected information, detection accuracy, or the like may be reduced.

According to some aspects of the invention, it is possible to provide an optical detection unit and a biological information detection device, capable of preventing light from a light emitting portion from being incident to a light receiving portion and minimizing deterioration in detection performance.

Solution to Problem

An aspect of the invention relates to an optical detection unit including a light emitting portion that emits light toward a target object; a light receiving portion that receives light from the target object; and a light blocking member that blocks light from being incident to at least the light receiving portion, in which the light blocking member includes a light blocking wall that is formed by performing sheet metal processing on a metal, and is provided between the light emitting portion and the light receiving portion so as to block light from the light emitting portion from being incident to the light receiving portion, in which the light blocking wall is formed of a first metal surface of the light blocking member.

In the aspect of the invention, light is emitted toward the target object by the light emitting portion, and light from the target object is received by the light receiving portion. In addition, the light blocking member which is formed by performing sheet metal processing on a metal is provided so as to block light from being incident to at least the light receiving portion. In this case, the light blocking wall which blocks light from the light emitting portion is formed of the first metal surface of the light blocking member which is formed through the sheet metal processing. If the light blocking wall is provided as mentioned above, it is possible to prevent light from the light emitting portion from being incident to the light receiving portion. In addition, if the light blocking member is formed through the sheet metal processing of a metal, it is possible to reduce a thickness of the metal surface while ensuring the strength or the like of the light blocking member. Therefore, the light blocking wall provided between the light emitting portion and the light receiving portion is formed of the first metal surface of the light blocking member which is formed through the sheet metal processing, and thus the thickness of the light blocking wall can be reduced compared with, for example, a case of forming the light blocking member through injection molding. As a result, the distance between the light emitting portion and the light receiving portion can be reduced, and thus it is possible to improve detection performance or the like of the optical detection unit while preventing light from the light emitting portion from being incident to the light receiving portion.

In the aspect of the invention, the light blocking member may be provided with a second metal surface and a third metal surface that are provided in a direction perpendicular to the first metal surface and form a light blocking wall which blocks light from being incident to the light receiving portion, a first end surface of the first metal surface may protrude further toward one side than an end surface of the second metal surface in a front view in which the first metal surface is viewed from the light emitting portion side, and a second end surface of the first metal surface opposing the first end surface may protrude further toward the other side which is different from one side than an end surface of the third metal surface in the front view.

With this configuration, light from the light emitting portion can be blocked by the first and second protruding end surfaces of the first metal surface, and thus it is possible to prevent a situation in which the light is incident to the light receiving portion.

In addition, in the aspect of the invention, the first metal surface and the second metal surface may be provided so as to be adjacent to each other via a first gap region, and the first metal surface and the third metal surface may be provided so as to be adjacent to each other via a second gap region.

When the first and second gap regions are provided in the configuration described above, it is possible to prevent a situation in which distortion or the like occurs in folded portions during sheet metal processing of the light blocking member, and thus folding processing is not smoothly performed. In addition, the first and second protruding end surfaces of the first metal surface can prevent a situation in which light is incident to the light receiving portion via the first and second gap regions.

Further, in the aspect of the invention, the light blocking member may include a fourth metal surface that is provided in a direction intersecting the first metal surface and blocks light from being incident to the light receiving portion, and the fourth metal surface may be provided with a diaphragm which restricts light from the target object on an optical path between the target object and the light receiving portion.

When the diaphragm is provided, it is possible to prevent stray light from the target object or the like from being incident to the light receiving portion, and thus to improve detection performance of the optical detection unit.

Still further, in the aspect of the invention, a distance LD between the light emitting portion and the light receiving portion may satisfy LD<3 mm.

With this configuration, the distance between the light emitting portion and the light receiving portion can be made shorter than in an optical detection unit of the related art, and thus it is possible to improve detection performance of the optical detection unit, such as sensitivity.

In addition, in the aspect of the invention, the distance LD may satisfy 0.3 mm<LD<2.5 mm.

With this configuration, the distance between the light emitting portion and the light receiving portion can be further reduced, and thus it is possible to improve detection performance such as sensitivity. In addition, if the distance LD is set to LD>0.3 mm, it is possible to prevent a situation in which a sufficient signal intensity of a detection signal cannot be obtained due to the absence of a target object in a range in which the optical detection unit can perform measurement.

Further, in the aspect of the invention, antireflection processing may be performed on at least an inner surface of the light blocking member.

With this configuration, it is possible to prevent a situation in which reflected light at the surface of the light blocking member strays and causes a noise component of a detection signal.

Still further, in the aspect of the invention, the light blocking member may not be provided on the light emitting portion and may be provided on the light receiving portion side.

With this configuration, it is possible to prevent a situation in which light emitted from the light emitting portion is blocked by the light blocking member, and thus an amount of light toward the target object is reduced. In addition, it is possible to prevent a situation in which a height of the light emitting portion side increases due to the light blocking member being provided on the light emitting portion side, and thus this impedes thinning of the optical detection unit.

In addition, in the aspect of the invention, the optical detection unit may further include a board on which the light emitting portion, the light receiving portion, and the light transmissive member are mounted, the light blocking member may include first and second projections that are engaged with holes of the board in order to fix the light blocking member to the board, and the first and second projections may be provided at positions which are linearly asymmetric to each other with respect to a central line of the light blocking member.

With this configuration, it is possible to prevent a situation in which the light blocking member is attached to the board at a wrong position and in a wrong direction when the light blocking member is attached to the board, and thus to simplify or efficiently perform assembling work of the optical detection unit.

Another aspect of the invention relates to a biological information detection device including any one of the optical detection units described above.

In addition, in another aspect of the invention, the biological information detection device may further include a light transmissive member that includes a convex portion which comes into contact with a subject and applies pressing to the subject during measurement of biological information of the subject which is the target object, and that transmits light incident to the light receiving portion and light emitted from the light emitting portion therethrough; and a pressing restricting portion that is provided so as to surround the convex portion and restricts the pressing which is applied to the subject by the convex portion.

With this configuration, it is possible to reduce a pressing change as a result of the pressing restricting portion restricting the pressing which is applied to the subject by the convex portion, and thus to improve detection performance or the like of the biological information detection device.

BRIEF DESCRIPTION OF DRAWINGS

FIGS. 7(A) to 7(C) are diagrams illustrating a connecting section of the biological information detection device.

DESCRIPTION OF EMBODIMENTS

Hereinafter, the present embodiment will be described. In addition, the present embodiment described below is not intended to improperly limit the content of the invention disclosed in the claims. Further, it cannot be said that all constituent elements described in the present embodiment are essential constituent elements of the invention.

1. Optical Detection Unit

Figure 1:
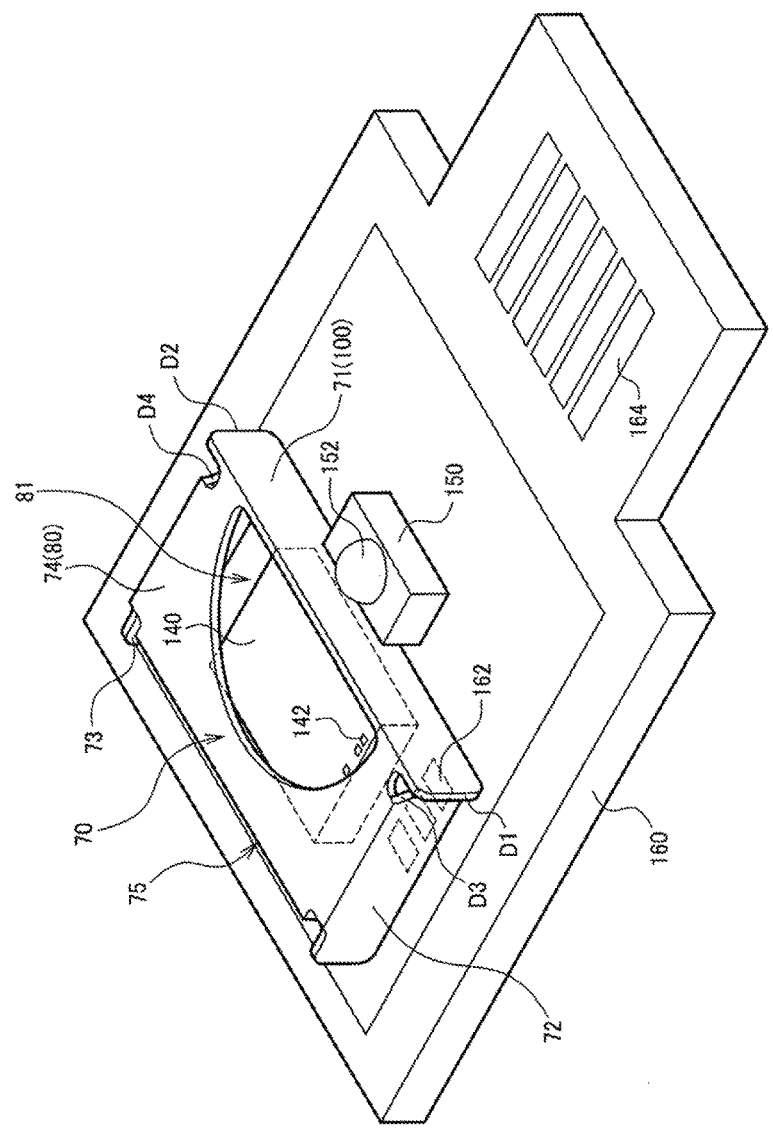
FIG. 1 is a perspective view illustrating a configuration example of an optical detection unit of the present embodiment.
Figure 2A:
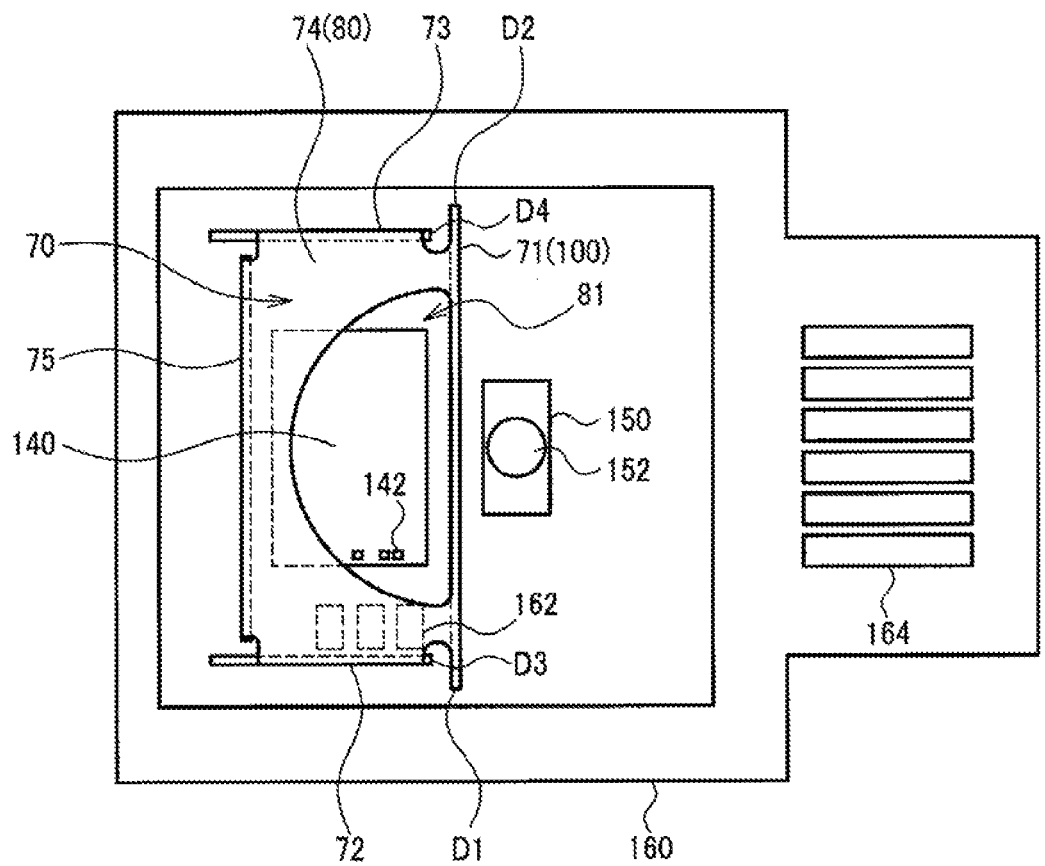
FIGS. 2(A) and 2(B) are respectively a plan view and a side view illustrating a configuration example of the optical detection unit of the present embodiment.
Figure 2B:
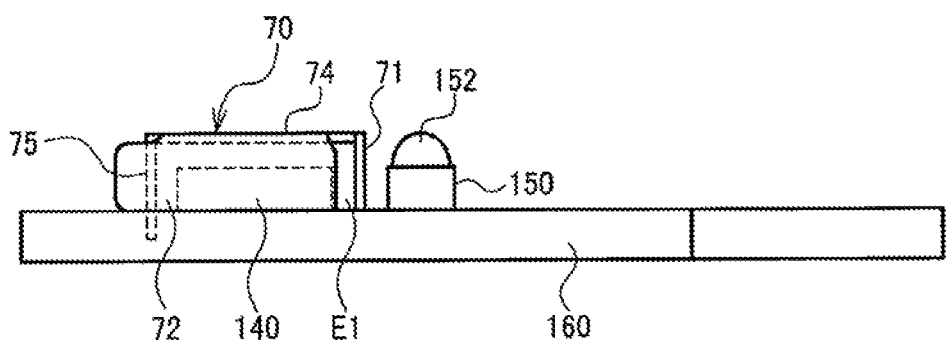

FIG. 1 is a perspective view illustrating a configuration example of an optical detection unit of the present embodiment, and FIGS. 2(A) and 2(B) are a plan view and a side view thereof.

The optical detection unit of the present embodiment includes a light receiving portion 140, a light emitting portion 150, and a light blocking member 70. In addition, a board 160 may be included.

The light emitting portion 150 emits light toward a target object (a subject or the like), and the light receiving portion 140 receives light from the target object. For example, if the light emitting portion 150 emits light, and the light is reflected by the target object, the light receiving portion 140 receives the reflected light. The light receiving portion 140 may be constituted of, for example, a light emitting element such as a photodiode. The light emitting portion 150 may be constituted of, for example, a light emitting element such as an LED. For example, the light receiving portion 140 may be constituted of a PN junction diode element or the like formed on a semiconductor substrate. In this case, an angle limiting filter for restricting a light reception angle or a wavelength limiting filter for limiting a wavelength of light which is incident to a light receiving element may be formed on the diode element.

For example, in a case where the optical detection unit is applied to a biological information detection device such as a pulsimeter, light from the light emitting portion 150 travels through the inside of a subject which is a target object and diffuses or scatters in the epidermis, the dermis, and the subcutaneous tissue. Then, the light reaches a blood vessel (detected site) and is reflected therefrom. At this time, some of the light is absorbed by the blood vessel. In addition, since an absorption rate of the light in the blood vessel changes due to an influence of the pulse and thus an amount of the reflected light also changes, the light receiving portion 140 receives the reflected light so as to detect the change in the amount of light, thereby detecting a pulse rate which is biological information.

In addition, a dome-shaped lens 152 (a condensing lens in a broad sense) provided in the light emitting portion 150 is a lens which collects light from an LED chip (a light emitting element chip in a broad sense) which is sealed with a resin (sealed with a light transmissive resin) in the light emitting portion 150. In other words, in the surface mounted light emitting portion 150, the LED chip is disposed under the dome-shaped lens 152, and light from the LED chip is collected by the dome-shaped lens 152 and is emitted to a target object. Consequently, it is possible to improve optical efficiency of the optical detection unit.

The light blocking member 70 is a member which blocks light. For example, in FIG. 1, the light blocking member 70 blocks light from being incident to the light receiving portion 140. In other words, the light blocking member 70 is not provided on the light emitting portion 150 side but is provided on the light receiving portion 140 side. For example, the light blocking member 70 is provided so as to cover the light receiving portion 140 and thus blocks light which is incident to the light receiving portion 140, but does not block light which is incident to the light emitting portion 150. However, there may be a modification example in which the light blocking member 70 is provided on the light emitting portion 150 side.

Antireflection processing is preferably performed on at least an inner surface of the light blocking member 70. For example, a color of a surface (the inner surface or the like) of the light blocking member 70 employs a predetermined color such as black, and thus irregular reflection of light is prevented. Alternatively, the surface of the light blocking member 70 may have a moth-eye structure. For example, an uneven structure with a cycle of several tens to several hundreds of nm is formed on the surface so as to obtain an antireflection structure. If such antireflection processing is performed, for example, it is possible to effectively prevent a situation in which reflected light at the surface of the light blocking member 70 strays and causes a noise component of a detection signal.

The light receiving portion 140, the light emitting portion 150, and the light blocking member 70 are mounted on the board 160. The board 160 is, for example, a rigid board. The board 160 is provided with terminals 162 which are connected to signal and power supply terminals 142 of the light receiving portion 140, and terminals 164 which are connected to signal and power supply terminals of an external main board. For example, the terminals 142 of the light receiving portion 140 are connected to the terminals 162 of the board 160 through wire bonding or the like.

In addition, in the present embodiment, the light blocking member 70 is formed by performing sheet metal processing on a metal (for example, an alloy of tin and copper). For example, the light blocking member 70 having a shape as illustrated in FIG. 1 and FIGS. 2(A) and 2(B) is formed by performing sheet metal processing on a single metal plate. In addition, the light blocking member 70 includes a light blocking wall 100 which is provided between the light emitting portion 150 and the light receiving portion 140. The light blocking wall 100 blocks light (direct light or the like) from the light emitting portion 150 from being incident to the light receiving portion 140. Further, the light blocking wall 100 is formed of a first metal surface 71 of the light blocking member 70 which is formed through the sheet metal processing. In other words, the first metal surface 71 as the light blocking wall 100 is provided between the light receiving portion 140 and the light emitting portion 150, and thus light from the light emitting portion 150 is prevented from being incident to the light receiving portion 140.

In addition, the light blocking member 70 includes second and third metal surfaces 72 and 73. The second and third metal surfaces 72 and 73 are provided in a direction intersecting (for example, perpendicular to) the first metal surface 71. For example, in a case where the first metal surface 71 is a metal surface on a front side, the second and third metal surfaces 72 and 73 are metal surfaces on lateral sides and serve as light blocking walls on the lateral sides.

In addition, as illustrated in FIGS. 1 and 2(A), a first end surface (left end surface) indicated by D1 of the first metal surface 71 protrudes further toward one side (left side) than an end surface indicated by D3 of the second metal surface 72 in a front view in which the first metal surface 71 is viewed from the light emitting portion 150 side. On the other hand, a second end surface (right end surface) indicated by D2, opposing the first end surface of the first metal surface 71 protrudes further toward the other side (right side) which is different from one side than an end surface indicated by D4 of the third metal surface 73 in the front view. In other words, the end surfaces which are respectively indicated by D1 and D2 of the first metal surface 71 protrude further toward both sides than the end surfaces indicated by D3 and D4 of the second and third metal surfaces.

For example, the first metal surface 71 and the second metal surface 72 are provided so as to be adjacent to each other via a first gap region indicated by E1 of FIG. 2(B). In addition, the first metal surface 71 and the third metal surface 73 are provided so as to be adjacent to each other via a second gap region. In other words, a rear surface of the first metal surface 71 and the end surfaces indicated by D3 and D4 of the second and third metal surfaces are not in contact with each other, and the gap region is present between the rear surface and the end surfaces.

Further, if such gap regions are present, there is a concern that light from the light emitting portion 150 may be incident to the light receiving portion 140 via the gap regions as will be described later in detail. However, in the present embodiment, as described above, the end surfaces indicated by D1 and D2 of the first metal surface 71 protrude further toward both sides than the second and third metal surfaces 72 and 73 in a front view, and thus it is possible to effectively prevent such a situation in which light from the light emitting portion 150 is incident to the light receiving portion 140.

In addition, the light blocking member 70 includes a fourth metal surface 74 which is provided in a direction intersecting (for example, perpendicular to) the first metal surface 71 and blocks light from being incident to the light receiving portion 140. The fourth metal surface 74 is, for example, an upper metal surface of the light blocking member 70.

In addition, a diaphragm 80 which restricts light (reflected light or the like) from a target object on an optical path between the target object and the light receiving portion 140 is formed on the fourth metal surface 74. In other words, an opening 81 of the diaphragm 80 is formed on the fourth metal surface 74. In addition, the light blocking member 70 is also provided with a fifth metal surface 75 serving as a light blocking wall of the rear surface thereof, and blocks light which is incident from the rear surface side.

2. Light Blocking Member 2.1 Sheet Metal Processing

The optical detection unit of the present embodiment is provided with the light blocking member 70 which blocks external light from being incident to the light receiving portion 140 or the like as illustrated in FIG. 1. In addition, the light blocking member 70 is formed by performing the sheet metal processing on a metal, and the light blocking wall 100 is constituted of, for example, the metal surface 71 of the light blocking member 70. The diaphragm 80 having the opening 81 is constituted of, for example, the metal surface 74 of the light blocking member 70. Here, the light blocking wall 100 has a wall surface, for example, in a direction intersecting (perpendicular to) a line segment which connects a central position of the light receiving portion 140 to a central position of the light emitting portion 150. Since the light blocking wall 100 is provided, light (direct light) from the light emitting portion 150 is prevented from being incident to the light receiving portion 140, and thus it is possible to improve reliability or the like of detection data.

That is, as will be described later in detail, as a distance between the light emitting portion 150 and the light receiving portion 140 becomes shorter, optical efficiency and performance of the optical detection unit is improved. For example, the optical efficiency and performance is reduced in inverse proportion to the square of the distance. Therefore, preferably, the distance between the light emitting portion 150 and the light receiving portion 140 is as short as possible.

On the other hand, if the distance between the light emitting portion 150 and the light receiving portion 140 is short, direct light from the light emitting portion 150 is incident to the light receiving portion 140, and thus a DC component increases and performance deteriorates. For this reason, in the optical detection unit of the present embodiment, the light blocking wall 100 is provided between the light receiving portion 140 and the light emitting portion 150.

In this case, as a technique of a comparative example of the present embodiment, there may be a technique of forming the light blocking member 70 through injection molding. The technique of the comparative example using the injection molding is a technique which is advantageous from the viewpoint of mass productivity of apparatuses or the like.

However, if the light blocking member 70 is formed through the injection molding, the light blocking wall 100 is thickened. In other words, if the light blocking wall 100 is designed so as to be thinned, the portion of the light blocking wall 100 is not sufficiently filled with a resin during the injection molding, and thus the light blocking wall 100 having a sufficient strength cannot be obtained. For this reason, in the technique of the comparative example using the injection molding, the thickness of the light blocking wall 100 becomes, for example, 0.4 mm or more.

In addition, if the light blocking wall 100 is thickened as mentioned above, the distance between the light emitting portion 150 and the light receiving portion 140 is also lengthened. As a result, for example, a length of an optical path between the light emitting portion 150 and the light receiving portion 140 via a target object increases, and thus the optical efficiency and performance of the optical detection unit deteriorate.

Figure 3:
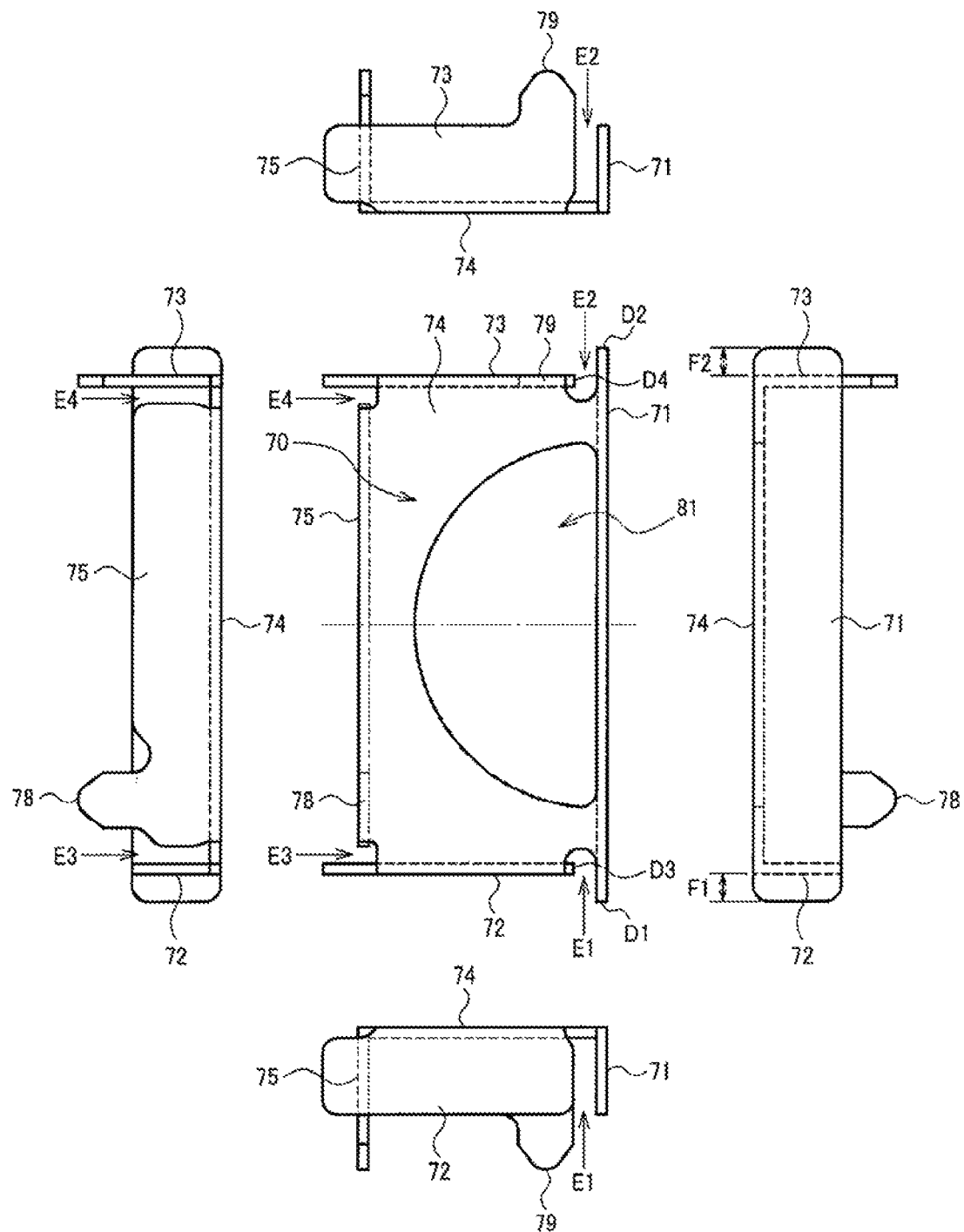
FIG. 3 shows a plan view, a side view, a front view, and a rear view illustrating a specific shape of a light blocking member.

Therefore, in the present embodiment, the light blocking member 70 is formed through sheet metal processing. For example, FIG. 3 shows a plan view, a side view, a front view, and a rear view illustrating a specific shape of the light blocking member 70. For example, if a single metal plate is folded through sheet metal processing, the light blocking member 70 formed of the metal surfaces 71, 72, 73, 74 and 75 is formed. Specifically, if the metal surfaces 71, 72, 73 and 75 are folded so as to be perpendicular (substantially perpendicular) to the metal surface 74 which is the upper surface, the light blocking member 70 is formed.

In addition, in FIG. 1, the metal surface 71 facing the light emitting portion 150 serves as the light blocking wall 100 which blocks direct light from the light emitting portion 150 from being incident to the light receiving portion 140. Further, the diaphragm 80 which restricts light from a target object on the optical path between the target object and the light receiving portion 140 is formed on the metal surface 74. In other words, the diaphragm 80 including the opening 81 is formed.

As mentioned above, if the light blocking wall 100 is implemented by using the metal surface 71 having undergone the sheet metal processing, the thickness of the light blocking wall 100 can be decreased more than in the technique of the comparative example using the injection molding. For example, in a case of using the sheet metal processing, it is possible to implement the light blocking member 70 having the sufficient strength even if the thickness of the metal surface is, for example, about 0.1 mm. For this reason, the thickness of the metal surface 71 serving as the light blocking wall 100 can be made, for example, about 0.1 mm. Therefore, the light blocking wall 100 can be sufficiently thinned compared with the technique of the comparative example using the injection molding which causes the thickness of the light blocking wall 100 to be, for example, 0.4 mm or more, and thus the distance between the light emitting portion 150 and the light receiving portion 140 can be shortened. Therefore, since the light blocking wall 100 can prevent direct light from the light emitting portion 150 from being incident to the light receiving portion 140, and an optical path length of light from the light emitting portion 150 to the light receiving portion 140 via a target object can be reduced, it is possible to improve detection performance and the like of the optical detection unit.

Particularly, in FIG. 1, the chip package type light emitting portion 150 is used. In the chip package type light emitting portion 150, for example, the dome-shaped lens 152 is disposed on the LED chip, and thus light emission efficiency toward a target object increases so that detection sensitivity of the optical detection unit can be increased.

However, the chip package type light emitting portion 150 has an arrangement occupation area larger than, for example, that of a light emitting portion in which an LED chip is disposed at a reflector. Therefore, there is a problem in that the distance between the light emitting portion 150 and the light receiving portion 140 is increased accordingly. In relation to this fact, according to the present embodiment, since the thickness of the light blocking wall 100 can be sufficiently reduced as described above, the problem can be solved even in a case of using the chip package type light emitting portion 150, and thus it is possible to improve detection performance of the optical detection unit, such as sensitivity.

In addition, in FIGS. 1 to 2(B), the light blocking member 70 is provided not on the light emitting portion 150 side but on the light receiving portion 140 side only. In other words, the light blocking member 70 covers the light receiving portion 140 so as to block light, but does not cover the light emitting portion 150.

For example, if the light blocking member 70 has such a shape that light is also blocked from being incident to the light emitting portion 150, some of light directed toward a target object from the light emitting portion 150 is blocked by the light blocking member 70, and thus there is a concern that an amount of light applied to the target object may be reduced so that detection performance such as sensitivity deteriorates.

In relation to this fact, as in FIGS. 1 to 2(B), if the light blocking member 70 has such a shape that light is blocked from being incident to the light receiving portion 140 side only, it is possible to prevent the occurrence of a situation in which light emitted from the light emitting portion 150 is blocked by the light blocking member 70 and thus an amount of light directed toward a target object is reduced.

Further, the configuration in which the light blocking member 70 is not provided on the light emitting portion 150 side and is provided only on the light receiving portion 140 side is advantageous from the viewpoint of thinning of the optical detection unit. For example, as illustrated in FIG. 2(B), the light emitting portion 150 provided with the dome-shaped lens 152 is higher than the light receiving portion 140. Thus, if the light blocking member 70 is provided on the light emitting portion 150 side, the height of the light emitting portion 150 side increases accordingly, and thus this impedes thinning of the optical detection unit.

In relation to this fact, in the configuration in which the light blocking member 70 is provided only on the light receiving portion 140 side, the light blocking member 70 is not present on the light emitting portion 150 side, and thus it is possible to align the height of the light receiving portion 140 side and the height of the light emitting portion 150 side with each other, for example, as illustrated in FIG. 2(B). Therefore, it is possible to reduce the entire height of the optical detection unit compared with a technique in which the light blocking member 70 is also provided on the light emitting portion 150 side, and thus to easily realize thinning of the optical detection unit.

In addition, as described above, the diaphragm 80 is provided in the light blocking member 70. In other words, the opening 81 is formed on the upper metal surface 74 of the light blocking member 70, and the diaphragm 80 is implemented by the opening 81. In this case, the opening 81 of the diaphragm 80 becomes more widely open as the opening becomes closer to the light emitting portion 150. For example, the opening 81 has a semicircular shape (a substantially semicircular shape), and a diameter of the semicircle is located on the light emitting portion 150 side. If the opening 81 of the diaphragm 80 has such a shape, light which is emitted from the light emitting portion 150 and is reflected by a target object can be made incident to the light receiving portion 140 with high efficiency, and thus detection performance such as sensitivity can be improved. Further, details of the diaphragm 80 will be described later.

2.2 Gap Region

In a case where the light blocking member 70 is formed through the sheet metal processing, a gap region is provided between the metal surface 71 and the metal surface 72 which are adjacent to each other as indicated by E1 of FIG. 3. In addition, as indicated by E2, a gap region is also provided between the metal surface 71 and the metal surface 73 which are adjacent to each other. Further, gap regions are also provided between the metal surface 75 and the metal surfaces 72 and 73 as indicated by E3 and E4. Unless such gap regions are provided, in a case where the metal surfaces 71, 72, 73 and 75 are folded with respect to the upper metal surface 74 through the sheet metal processing, there is a problem in that distortion or the like occurs in the folded portions, and thus folding processing is not smoothly performed.

In relation to this problem, as indicated by E1, E2, E3, and E4 of FIG. 3, if the gap regions are provided, and folded corner portions of the metal surfaces are made to have, for example, curved shapes (R shapes), it is possible to prevent the occurrence of such a problem.

However, if the gap regions as indicated by E1 and E2 are formed, for example, light from the light emitting portion 150 is incident to the light receiving portion 140 through the gap regions, and, as a result, there is a concern that a DC component or the like caused by direct light may increase, and thus performance thereof may deteriorate.

Therefore, in the present embodiment, the light blocking member 70 is formed so that the end surfaces indicated by D1 and D2 of the metal surface 71 of FIG. 3 protrude further toward both sides than the end surfaces indicated by D3 and D4 of the metal surfaces 72 and 73 in a front view which is viewed from the light emitting portion 150 side (a front view in a direction perpendicular to the metal surface 71). For example, the end surface indicated by D1 of the metal surface 71 protrudes further toward the left side (one side) than the end surface indicated by D3 of the metal surface 72, and the end surface indicated by D2 of the metal surface 71 protrudes further toward the right side (the other side) than the end surface indicated by D4 of the metal surface 73. In other words, protruding portions as indicated by F1 and F2 of FIG. 3 are formed so as to extend in the metal surface 71.

In the above-described way, even in a case where the gap regions indicated by E1 and E2 are formed, direct light from the light emitting portion 150 is blocked by the protruding portions indicated by F1 and F2 of the metal surface 71 and thus is not incident to the light receiving portion 140. In other words, there is a possibility that external light other than the direct light may be incident from the gap regions, but at least the direct light from the light emitting portion 150 is not incident to the light receiving portion 140 due to the protruding portions of the metal surface 71 serving as barriers.

Therefore, if the gap region is formed at a boundary between the respective sides of the metal surfaces, both of the two problems can be solved together since inconvenience in folding during the sheet metal processing can be removed, and deterioration in the detection performance can be prevented as a result of preventing incidence of direct light due to the presence of the gap region.

In addition, a positional relationship between or shapes of the end surfaces indicated by D1 and D2 of the metal surface 71 and the end surfaces indicated by D3 and D4 of the metal surfaces 72 and 73 are not limited to the positional relationship or shapes illustrated in FIG. 3. In other words, as long as, as indicated by at least F1 and F2, the protruding portions for the end surfaces indicated by D3 and D4 are formed so as to extend in the metal surface 71, and thus a positional relationship occurs or shapes thereof are formed so that light from the light emitting portion 150 is blocked by the protruding portions, various modification examples may occur.

Further, as illustrated in FIG. 1 described above, the light emitting portion 150, the light receiving portion 140, and the light blocking member 70 are mounted on the board 160. Still further, as illustrated in FIG. 3, the light blocking member 70 includes projections 78 and 79 (first and second projections). In other words, the light blocking member 70 includes the projections 78 and 79 for fixation to the board 160. The projections 78 and 79 are engaged with holes formed at the board 160, and thus the light blocking member 70 is fixed to the board 160.

Specifically, in FIG. 3, the projection 78 is formed in the rear metal surface 75, and the projection 79 is formed in the right metal surface 73. In this case, positions and shapes of the projections 78 and 79 are not linearly symmetric to each other with respect to a central line CL of the light blocking member 70, that is, linearly asymmetric to each other. For example, the projections 78 and 79 are not provided at positions which are linearly symmetric to each other with respect to the central line CL and are provided at positions which are linearly asymmetric to each other. Here, the central line CL corresponds to, for example, a line which connects a central position of the light receiving portion 140 to a central position of the light emitting portion 150. In addition, directions of surfaces of the projections 78 and 79 are not also linearly symmetric to each other with respect to the central line CL. For example, the surface of the projection 78 is located in a direction perpendicular to the central line, and the surface of the projection 79 is located in a direction of the central line.

As mentioned above, if the projections 78 and 79 have such linearly asymmetric positions and shapes, it is possible to prevent a situation in which the light blocking member 70 is attached to the board 160 at a wrong position and in a wrong direction when the light blocking member 70 is attached to the board 160. Therefore, it is possible to simplify or efficiently perform assembling work of the optical detection unit and thus to realize cost reduction or the like. In addition, in the present embodiment, since the light blocking member 70 is formed through the sheet metal processing, there is an advantage in that the projections 78 and 79 having the linearly asymmetric positions and shapes can be easily formed. In other words, as illustrated in FIG. 3, if the projection 78 is formed, for example, on the left side of the rear metal surface 75, and the projection 79 is formed, for example, on the front side of right metal surface 73, it is possible to implement the projections 78 and 79 having the linearly asymmetric positions and shapes.

2.3 Distance Between Light Emitting Portion and Light Receiving Portion

Figure 4:
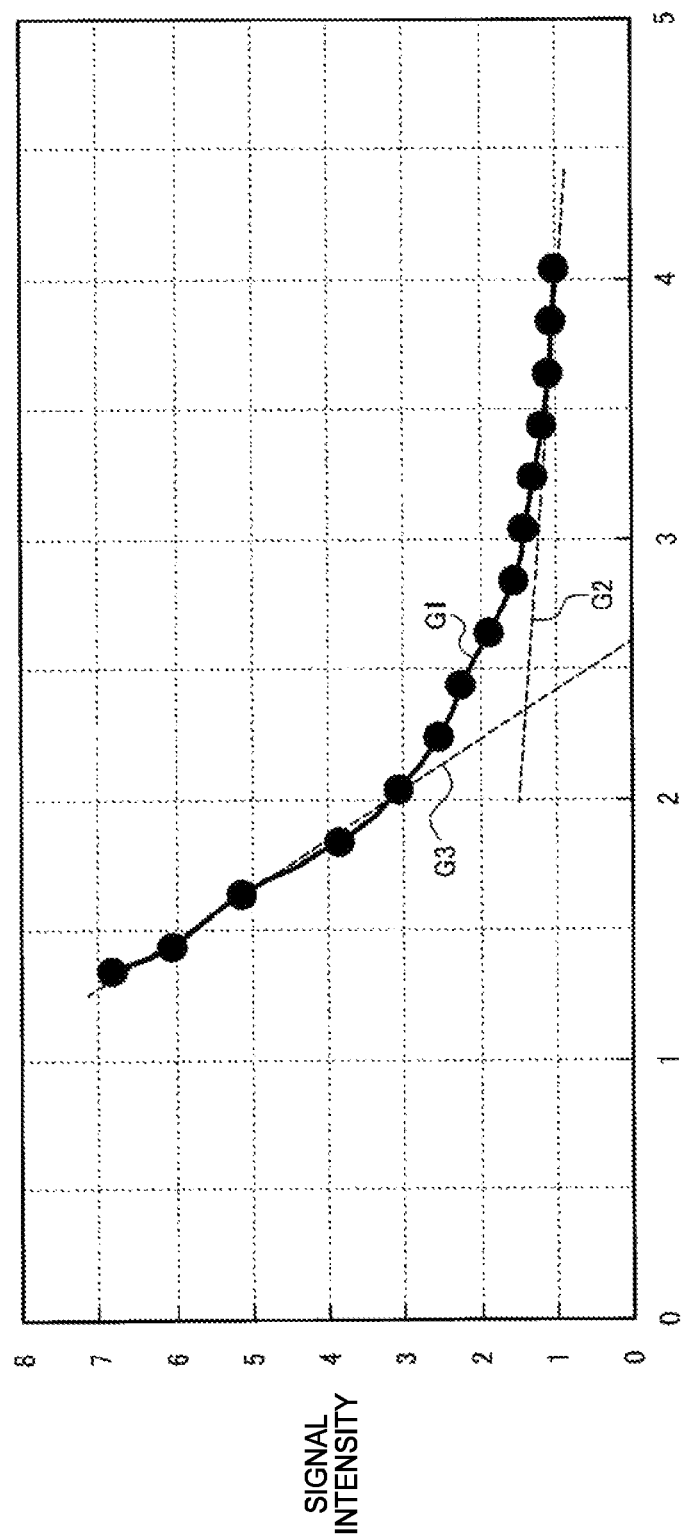
FIG. 4 is a diagram illustrating a relationship between a distance from a light emitting portion and a light receiving portion and the intensity of a detection signal.

FIG. 4 is a diagram illustrating a relationship between a distance LD from the light emitting portion 150 to the light receiving portion 140 and a signal intensity. Here, the signal intensity is an intensity of a detection signal for a detection device which employs the optical detection unit of the present embodiment. For example, in a case where the optical detection unit is applied to a detection device of biological information such as a pulse wave as will be described later, the signal intensity is an intensity of a detection signal of biological information such as a pulse wave. In addition, the distance LD between the light emitting portion 150 and the light receiving portion 140 is, for example, a distance between central positions (representative positions) of the light emitting portion 150 and the light receiving portion 140. For example, in a case where the light receiving portion 140 has a rectangular shape (substantially rectangular shape), a position of the light receiving portion 140 is a central position of the rectangular shape. Further, in a case where the light emitting portion 150 includes the above-described dome-shaped lens 152, a position of the light emitting portion 150 is, for example, a central position (a position of the LED chip) of the dome-shaped lens 152.

As is clear from FIG. 4, as the distance LD between the light emitting portion 150 and the light receiving portion 140 is reduced, the signal intensity of a detection signal increases, and detection performance such as sensitivity increases. Therefore, the distance LD between the light emitting portion 150 and the light receiving portion 140 becomes preferably smaller.

In relation to this fact, in the present embodiment, as illustrated in FIGS. 1 to 3 described above, the light blocking member 70 is formed through the sheet metal processing, and the light blocking wall 100 is formed of the metal surface 71. Therefore, when compared with a case where the light blocking member 70 is formed through the injection molding, the thickness of the light blocking wall 100 can be reduced, and may be, for example, about 0.1 mm. Therefore, the distance LD between the light emitting portion 150 and the light receiving portion 140 can be shortened by the reduced thickness of the light blocking wall 100, and thus detection performance of a detection device can be improved as is clear from FIG. 4.

In this case, as illustrated in FIG. 4, the distance between the light receiving portion 140 and the light emitting portion 150 is preferably LD<3 mm. For example, as is clear from a tangential line G2 of a longer distance side in a characteristic curve G1 illustrated in FIG. 4, the characteristic curve G1 is saturated in a range of LD 3 mm. In contrast, in a range of LD<3 mm, as the distance LD becomes shorter, the signal intensity considerably increases. Therefore, in this meaning, the distance is preferably LD<3 mm.

In addition, the distance LD is preferably LD<2.5 mm. For example, as understood from a relationship between the tangential line G2 of the longer distance side and the tangential line G3 of the shorter distance side, an increase ratio of the signal intensity to the distance is further heightened in a range of the distance LD<2.5 mm (2.4 mm). Therefore, in this meaning, the distance is more preferably LD<2.5 mm.

In addition, in the optical detection unit of the present embodiment illustrated in FIGS. 1 to 3, for example, the distance LD is LD=about 2.0 mm. Therefore, as illustrated in FIG. 4, detection performance can be considerably improved compared with an optical detection unit of the related art in which the distance LD is LD≥3 mm.

Figure 5:
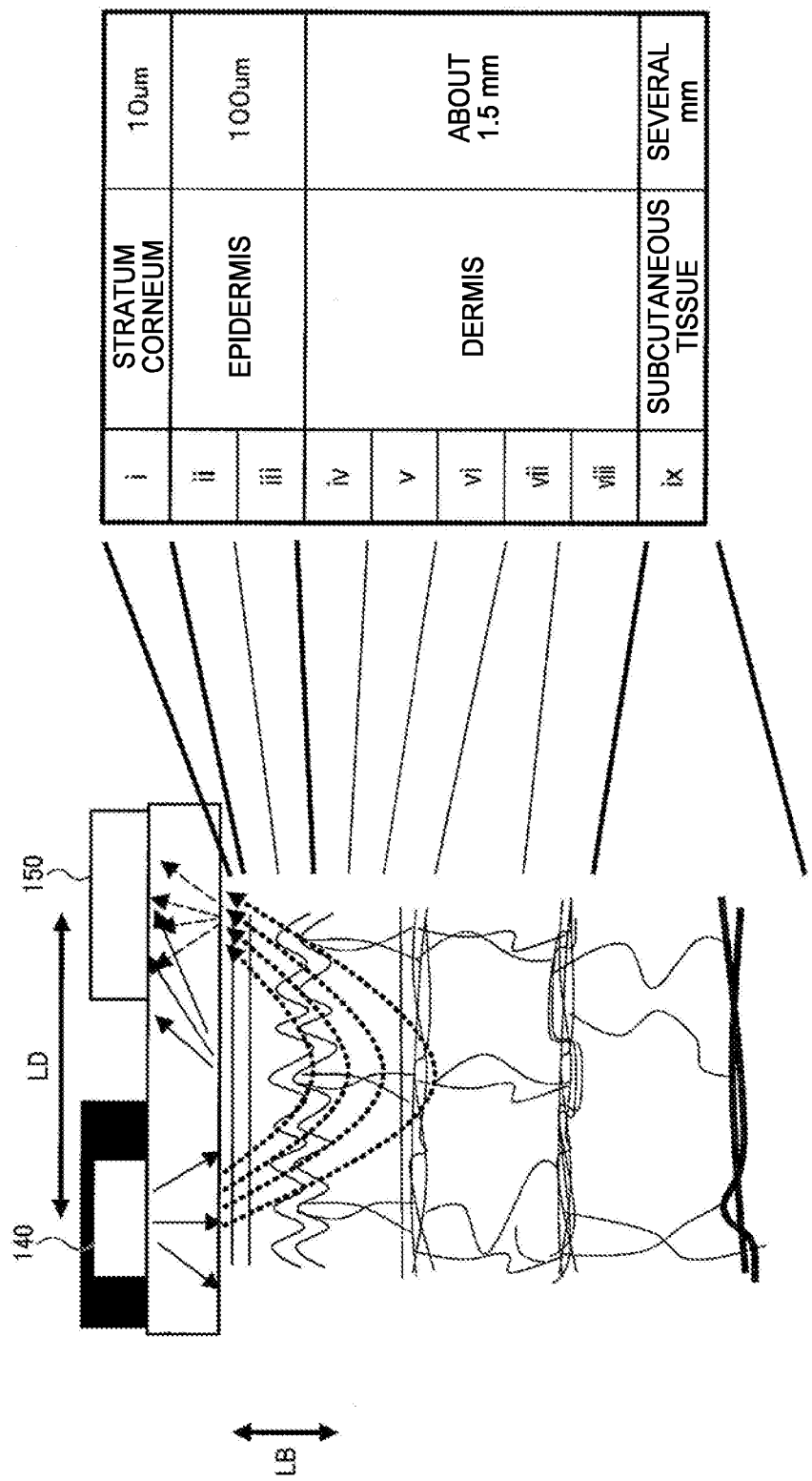
FIG. 5 is a diagram illustrating a relationship between the distance from the light emitting portion to the light receiving portion and a measured distance in a depth direction.

Further, the distance LD has a lower limit value, and thus it is not preferable to make the distance LD too short. For example, FIG. 5 is a diagram illustrating a case where the optical detection unit of the present embodiment is applied to a detection device of biological information such as a pulse wave. In this case, light from the light emitting portion 150 diffuses or scatters in a blood vessel or the like of a subject, and the light is incident to the light receiving portion 140 so that a pulse wave is detected. In addition, in FIG. 5, a relationship of LD=2×LB is generally established between the distance LD between the light emitting portion 150 and the light receiving portion 140 and a measurement distance LB in a depth direction. For example, a measurement limit distance in the optical detection unit constituted of the light emitting portion 150 and the light receiving portion 140 which are separated from each other by the distance LD is about LB=LD/2. Further, there is no blood vessel which is a detection target object of a pulse wave in a range in which the distance LB is 100 µm to 150 µm, for example. Therefore, if the distance LD is LD≤2×LB=2×100 to 2×150 µm=0.2 mm to 0.3 mm, an intensity of a detection signal of a pulse wave is expected to be considerably reduced. In other words, if the distance LD becomes shorter, the measurement distance LB in the depth direction is reduced in proportion thereto. Therefore, if there is no detection target object in a range of the distance LB, an intensity of a detection signal is considerably reduced. In other words, as the distance LD becomes shorter, detection performance is improved, but there is a limit therein, and a lower limit value is present. Therefore, in this meaning, the distance is LD>0.3 mm. In other words, preferably, the distance is 0.3 mm<LD<2.5 mm (or 0.3 mm<LD<3.0 mm).

3. Biological Information Detection Device

Figure 6A:
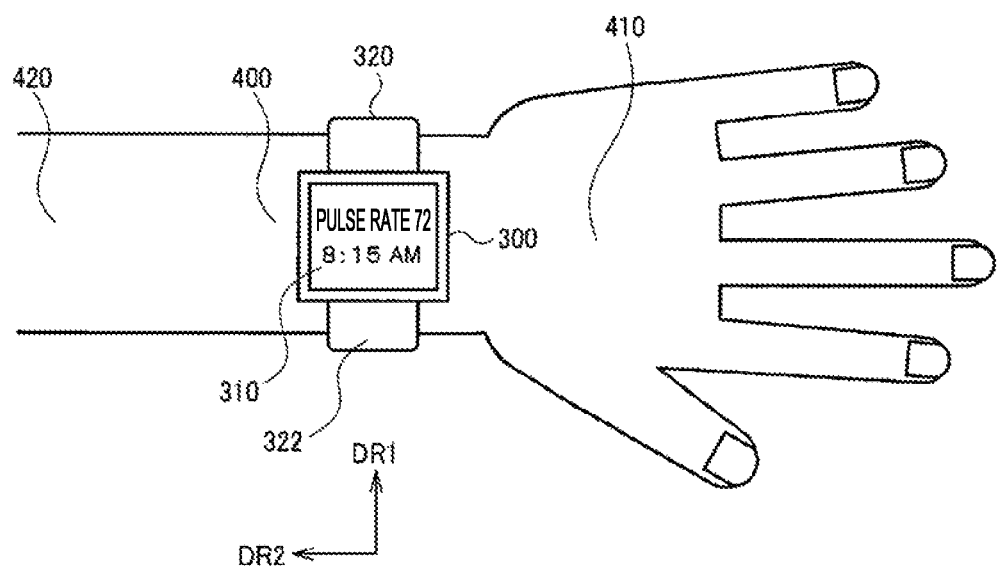
FIGS. 6(A) and 6(B) are exterior views of a biological information detection device of the present embodiment.

FIG. 6(A) is an exterior view illustrating an example of a biological information detection device (biological information measurement device) including the optical detection unit of the present embodiment. The biological information detection device is a wristwatch type pulsimeter, and includes a main body section 300 and bands 320 and 322 (wrist bands) for mounting the biological information detection device on the wrist 400 of a subject. The main body section 300 which is a device main body is provided with a display portion 310 which displays various kinds of information, a pulse wave sensor (a sensor constituted of a detector, a light transmissive member, and the like; the optical detection unit), a processing portion which processes various processes, and the like. The display portion 310 displays a measured pulse rate or the time. In addition, in FIG. 6(A), a circumferential length direction of the wrist 400 (or the arm) is set to a first direction DR1, and a direction which is directed from the hand 410 toward the lower arm 420 is set to a second direction DR2.

Figure 6B:
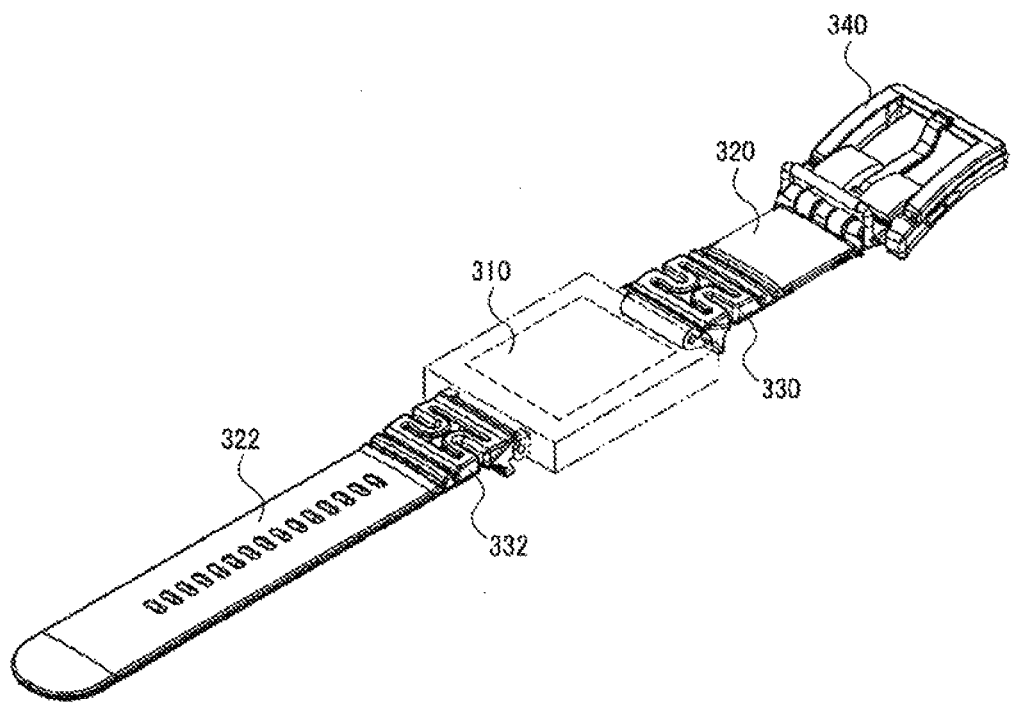

FIG. 6(B) is an exterior view illustrating a specific configuration example of the biological information detection device. The bands 320 and 322 are connected to the main body section 300 via extendable portions 330 and 332. The extendable portions 330 and 332 can be deformed in the first direction DR1 and the second direction DR2 illustrated in FIG. 6(A). One end of the band 320 is connected to a connecting portion 340. The connecting portion 340 corresponds to a buckle of a watch, and band holes into which a rod of the buckle is inserted are formed at the opposite band 322.

As illustrated in FIG. 7(A), the connecting portion 340 includes a fixation member 342 fixed to the band 320, a sliding member 344, and springs 350 and 352 which are elastic members. In addition, as illustrated in FIGS. 7(B) and 7(C), the sliding member 344 is attached to the fixation member 342 so as to slide in a sliding direction DRS, and the springs 350 and 352 generate tensile forces during sliding. A load mechanism of the present embodiment is constituted of the springs 350 and 352, the extendable portions 330 and 332, the bands 320 and 322, and the like.

The fixation member 342 is provided with an indicator 343, and points P1 and P2 indicating an appropriate sliding range (pressing range) are added to the indicator. If an end of the sliding member 344 on the band 320 side is located within the range of the points P1 and P2, it is ensured that an appropriate tensile force acts within the appropriate sliding range (pressing range). A user inserts the rod of the connecting portion 340 as a buckle into the band hole of the band 322 so that the appropriate sliding range is obtained, and mounts the biological information detection device on the user's wrist. In this way, it is ensured to an extent that pressing of the pulse wave sensor (a convex portion of the light transmissive member) toward the subject becomes expected appropriate pressing.

In addition, in FIGS. 6(A) to 7(C), as an example, a description has been made of a case where the biological information detection device is a wristwatch type pulsimeter which is mounted on the wrist, but the present embodiment is not limited thereto. For example, the biological information detection device of the present embodiment may be mounted on parts (for example, the finger, the upper arm, and the chest) other than the wrist, and may detect (measure) biological information. Further, biological information which is a detection target of the biological information detection device is not limited to a pulse wave (pulse rate), and the biological information detection device may be a device which detects biological information (for example, oxygen saturation in blood, a body temperature, and a heartbeat) other than a pulse wave.

Figure 8:
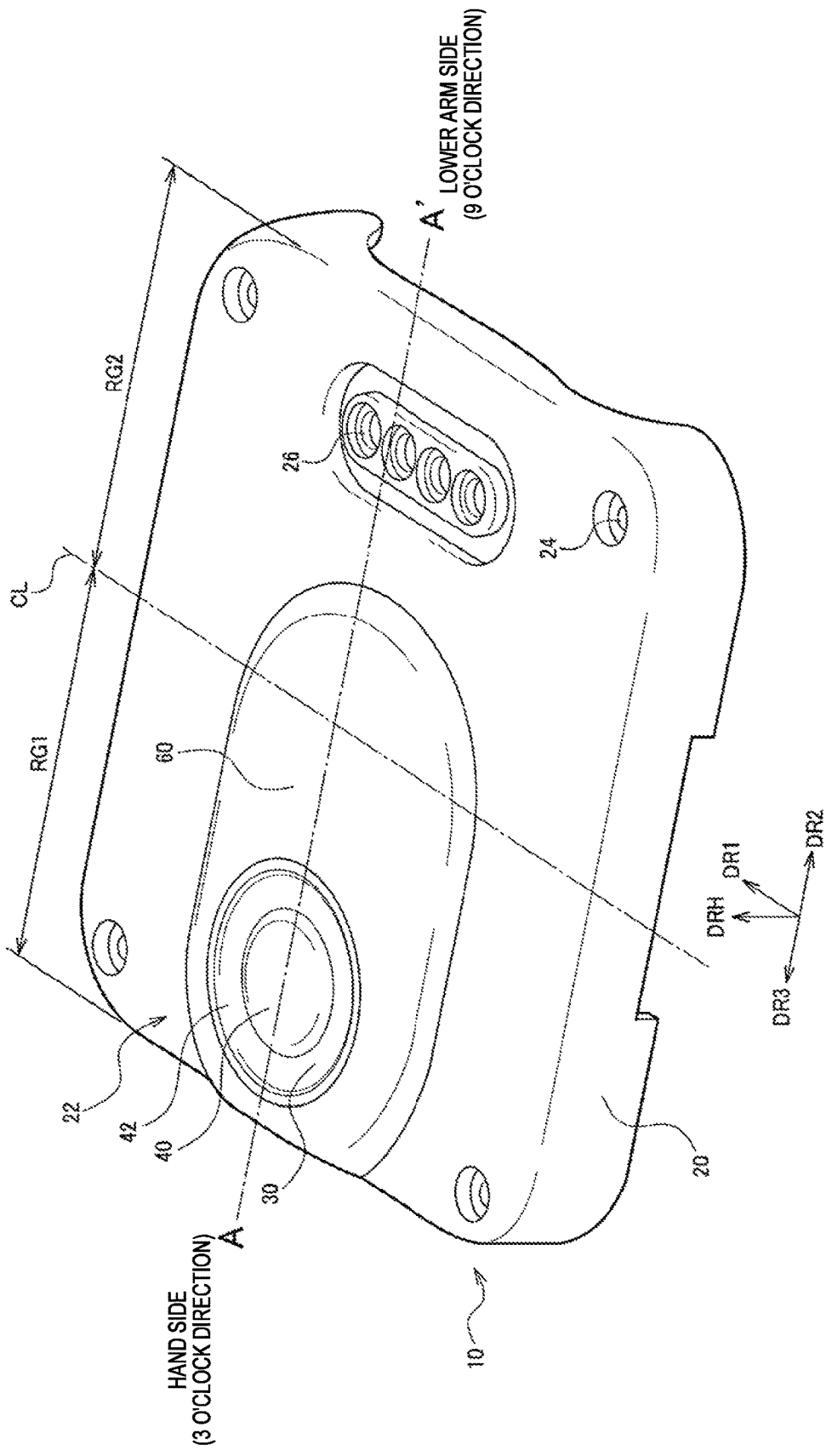
FIG. 8 is a perspective view illustrating a rear cover of a main body section of the biological information detection device.
Figure 9:
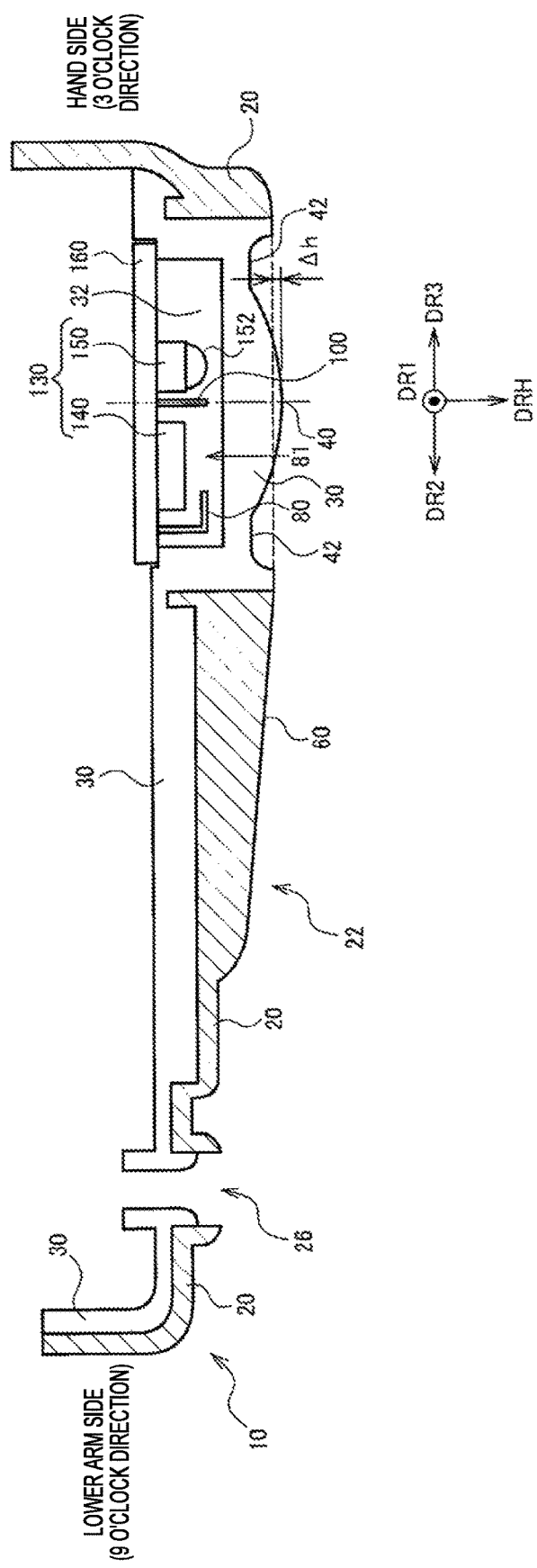
FIG. 9 is a sectional view illustrating the rear cover.

FIG. 8 is a perspective view illustrating a configuration example of a rear cover 10 provided on the back of the main body section 300 of the biological information detection device, and FIG. 9 is a sectional view taken along the line A-A' of FIG. 8. The rear cover 10 is constituted of a cover member 20 and a light transmissive member 30, and a rear casing surface 22 (rear surface) of the main body section 300 is formed of the rear cover 10.

The light transmissive member 30 is provided on the casing surface 22 side of the biological information detection device which is in contact with a subject (a target object in a broad sense). In addition, the light transmissive member transmits incident light (light from the subject) to the light receiving portion 140 therethrough. Further, the light transmissive member transmits light emitted from the light emitting portion 150 therethrough. Still further, the light transmissive member 30 is in contact with the subject during measurement of biological information of the subject. For example, the light transmissive member 30 includes a convex portion 40 which comes into contact with the subject and applies pressing to the subject during measurement of biological information of the subject. Furthermore, a surface shape of the convex portion 40 is preferably a curved shape (a spherical shape), but is not limited thereto, and various shapes may be employed. Moreover, the light transmissive member 30 may be optically transparent to a wavelength of light from the subject, may be formed by using a transparent material, and may be formed by using a colored material.

As illustrated in FIG. 9, the cover member 20 is formed so as to cover the light transmissive member 30. The light transmissive member 30 is transmissive, but the cover member 20 is not a transmissive member but a non-transmissive member. For example, the light transmissive member 30 is made of a transparent resin (plastic), and the cover member 20 is made of a resin in a predetermined color such as black. In addition, the non-transmissive member indicates a member which does not transmit light with a wavelength which can be detected by the biological information detection device therethrough.

Further, as illustrated in FIGS. 8 and 9, a part of the light transmissive member 30 is exposed to the subject side from an opening of the cover member 20, and the convex portion 40 is formed at this exposed portion. Therefore, the convex portion 40 formed at the exposed portion comes into contact with the subject (for example, a skin of the wrist of the user) during measurement of biological information. In FIGS. 8 and 9, a detection window of the biological information detection device is constituted of the convex portion 40 formed at the exposed portion. Here, in FIG. 9, the light transmissive member 30 is also provided on portions other than the detection window, that is, a rear portion of the cover member 20 (a pressing restriction portion 60). However, the present embodiment is not limited thereto, and the light transmissive member 30 may be provided only at the detection window portion.

In addition, as illustrated in FIG. 9, a groove 42 for minimizing a pressing change or the like is provided around the convex portion 40. Further, assuming that a surface of the light transmissive member 30 on which the convex portion 40 is provided is a first surface, the light transmissive member 30 includes a concave portion 32 at a position corresponding to the convex portion 40 on a second surface which is a rear surface of the first surface. Still further, the rear cover 10 is provided with screw holes 24 to which the rear cover 10 is screwed, terminal holes 26 to which terminals for transmitting signals or supplying power are connected, and the like.

As illustrated in FIG. 8, in a case where the casing surface 22 (rear surface) of the biological information detection device is divided into a first region RG1 and a second region RG2 by the central line CL which is located in the first direction DR1, the convex portion 40 is provided in the first region RG1. If the biological information detection device of a type mounted on the wrist as illustrated in FIG. 6(A) is exemplified, the first region RG1 is a region on the hand side (the three o'clock direction in the watch), and the second region RG2 is a region on the lower arm side (a nine o'clock direction in the watch). As mentioned above, the convex portion 40 of the light transmissive member 30 is provided in the first region RG1 which is close to the hand on the casing surface 22. In the above-described way, the convex portion 40 is disposed in a location where a change in the diameter of the arm is small, and thus a pressing change or the like can be minimized.

In addition, the convex portion 40 comes into contact with a subject and applies pressing (pressing force) to the subject during measurement of biological information of the subject. Specifically, when the user mounts the biological information detection device on the wrist, and biological information such as a pulse wave is detected, the convex portion 40 comes into contact with the skin of the user's wrist so as to apply pressing. This pressing is generated due to a load caused by the load mechanism described in FIGS. 6(A) to 7(C).

In addition, the casing surface 22 of the biological information detection device is provided with a pressing restricting portion 60 which restricts pressing which is applied to the subject (the skin of the wrist) by the convex portion 40. In FIGS. 8 and 9, the pressing restricting portion 60 is provided so as to surround the convex portion 40 of the light transmissive member 30 on the casing surface 22. Further, the surface of the cover member 20 functions as the pressing restricting portion 60. In other words, the surface of the cover member 20 is molded in a bank shape so that the pressing restricting portion 60 is formed. As illustrated in FIG. 9, a pressing restricting surface of the pressing restricting portion 60 is tilted so as to be lowered from the position of the convex portion 40 in the second direction DR2 (the direction from the wrist toward the lower arm). In other words, the pressing restricting surface is tilted so that a height in a direction DRH perpendicular to the casing surface 22 is reduced in the second direction DR2.

Further, in FIGS. 8 and 9, a detector 130 or the convex portion 40 (detection window) is provided in the first region RG1 on the hand side (three o'clock direction) of the casing surface 22 (rear surface), but the present embodiment is not limited thereto. For example, the detector 130 or the convex portion 40 (detection window) may be provided in a central region (a region through which the central line CL passes) of the casing surface 22, and the pressing restricting portion 60 may be provided therearound.

As illustrated in FIG. 9, the detector 130 is provided in a lower direction of the convex portion 40 of the light transmissive member 30. Here, an upper direction is the direction DRH, and the lower direction is a direction opposite to the direction DRH. In other words, the lower direction is a direction which is directed from a rear surface (a surface on a side which comes into contact with the subject) of the main body section 300 of the biological information detection device toward a front surface (a surface on a side which does not come into contact with the subject).

The detector 130 constitutes the optical detection unit of the present embodiment, and includes the light receiving portion 140 and the light emitting portion 150. In addition, details of the light receiving portion 140 and the light emitting portion 150 have been described, and thus detailed description will be omitted here.

Further, in the present embodiment, as illustrated in FIG. 9, the light blocking wall 100 (a light blocking portion) is provided between the light receiving portion 140 and the light emitting portion 150, and the light blocking wall 100 prevents direct light from the light emitting portion 150 from being incident to the light receiving portion 140. The light blocking wall 100 is formed of the metal surface 71 of the light blocking member 70 illustrated in FIG. 1. Further, the diaphragm 80 including the opening 81 is provided on the light receiving portion 140 side. The diaphragm 80 restricts light from a subject on the optical path between the subject and the light receiving portion 140. The diaphragm 80 is formed of the metal surface 74 of the light blocking member 70 illustrated in FIG. 1.

4. Diaphragm

Meanwhile, in the biological information detection device described in FIGS. 6(A) to 9, the surface of the light transmissive member 30 which comes into contact with a subject's skin is a contact surface having a finite area. In addition, for example, an object which is relatively smooth, such as a skin, is brought into contact with the contact surface having a finite area of the light transmissive member 30 which is made of a rigid material such as a resin or glass. Then, in terms of elastodynamics, a region which is not in contact with the skin or a region where a contact pressure is weak is generated in the vicinity of a circumferential edge (outer circumference) of the light transmissive member 30. Further, the region around the circumferential edge of the contact surface is likely to float, for example, when an external force is applied to a device such as the biological information detection device and thus a moment is generated in the device.

An optical difference between light intensities occurs in light which passes through the light emitting portion 150, the skin, and the light receiving portion 140 via the region due to a change in a dynamic contact state. In addition, if such light is incident to the light receiving portion 140, the light becomes noise having no relation to a pulse component.

Further, deterioration in signal quality may occur even in a static contact state. If the contact surface does not come into proper contact with the skin, external light which does not originate in the light emitting portion 150 may be incident to the light receiving portion 140. On the other hand, in a case where the contact surface comes into excessive contact with the skin, blood vessels under the skin are crushed, and thus light passing through the region is unlikely to include a pulsation component.

If such noise is considerably superimposed, quality of a pulse wave detection signal is reduced, and reliability of measured data deteriorates in various types of biological information measurement such as pulse measurement.

Figure 10B:
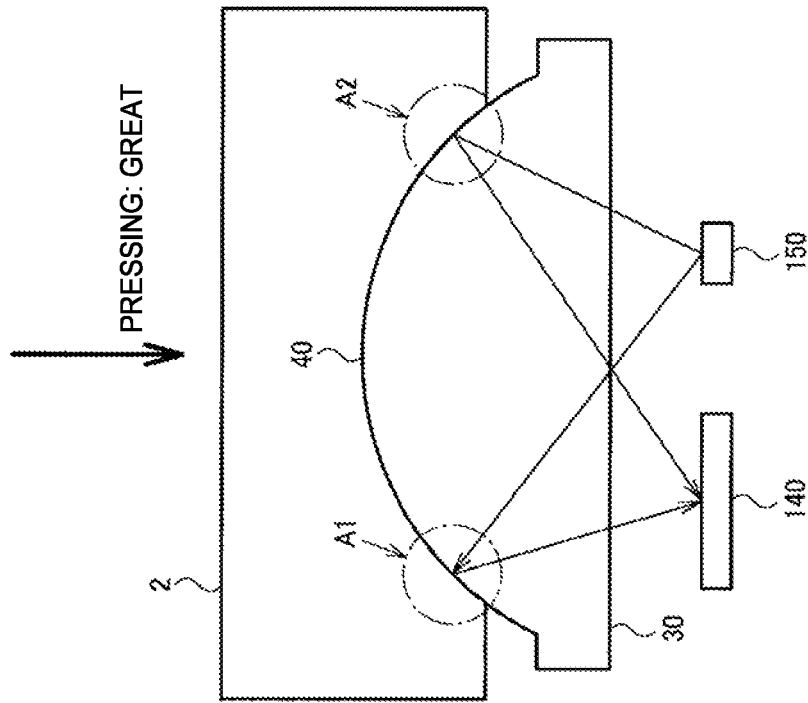
FIGS. 10(A) and 10(B) are diagrams for explaining problems when pressing of a light transmissive member for a subject changes.
Figure 10A:
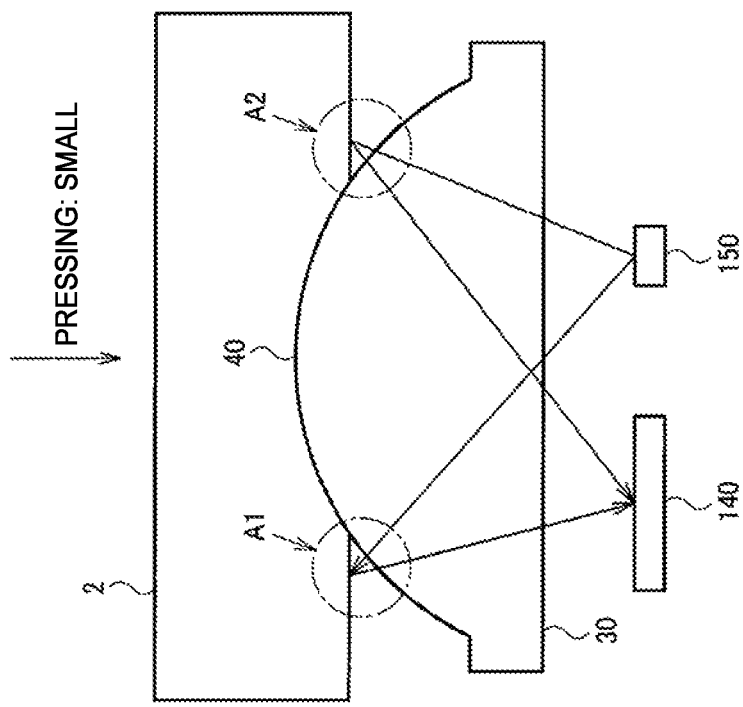

For example, FIG. 10(A) illustrates a case where pressing which is applied to a subject' skin 2 by the convex portion 40 (contact surface) of the light transmissive member 30 is slight, and FIG. 10(B) illustrates a case where the pressing is considerable. Looking at locations indicated by A1 and A2 of FIGS. 10(A) and 10(B), a contact state between the skin 2 and the convex portion 40 changes due to a pressing change. In the locations indicated by A1 and A2, for example, the skin 2 and the convex portion 40 are brought into a noncontact state or a weak contact state in FIG. 10(A), but are brought into a contact state in FIG. 10(B). Therefore, intensities of light which is emitted from the light emitting portion 150 and is returned to the light receiving portion 140 are different between FIGS. 10(A) and 10(B), and thus reliability of measured data deteriorates. In other words, in the locations indicated by A1 and A2 of FIGS. 10(A) and 10(B), pressing on the contact surface rapidly changes due to a minute change in a load, and thus reliability of measured data considerably deteriorates.

For example, in FIGS. 10(A) and 10(B), the contact surface of the light transmissive member 30 which comes into contact with a skin of a human body is formed in a curved convex shape (convex portion). In the above-described way, a degree of adhesion of the light transmissive member 30 to a skin surface is improved, and thus it is possible to prevent entrance of noise light such as light reflected from the skin surface or disturbance light.

However, a contact pressure with the skin is reduced at a circumferential edge (outer circumference) of the convex shape more than at a center thereof. In this case, if optimization to the contact pressure at the center is performed, the contact pressure at the circumferential edge is lower than the optimal range. On the other hand, if optimization to the contact pressure at the circumferential edge is performed, the contact pressure at the center exceeds the optimal range.

In a case where the contact pressure is lower than the optimal range, the pulse wave sensor may be brought into contact with or be separated from the skin due to shaking of the device, or body movement noise may be superimposed on a pulse wave detection signal since the pulse wave sensor does not crush the vein even in the contact state. If such a noise component is reduced, it is possible to obtain a pulse wave detection signal showing a higher M/N ratio (S/N ratio). Here, M indicates a level of the pulse wave detection signal, and N indicates a noise level.

In order to solve the above-described problems, in the present embodiment, the diaphragm 80 as illustrated in FIGS. 1 and 9, and the like are provided. In other words, the diaphragm 80 is provided and restricts light so that light (stray light) is not detected at the locations indicated by A1 and A2 of FIGS. 10(A) and 10(B). For example, light passing through a center of a light transmissive region (for example, the top of the convex portion) of the light transmissive member 30 which is optimally pressed is transmitted without being blocked if at all possible, whereas light passing through the vicinity of the circumferential edge of the light transmissive region (for example, the convex portion) of the light transmissive member 30 is blocked. In the above-described way, as illustrated in FIGS. 10(A) and 10(B), even in a case where contact states change at the locations indicated by A1 and A2, states of light at the locations indicated by A1 and A2 do not influence light receiving results. Therefore, it is possible to improve reliability or the like of measured data.

In addition, in the above description, a description has been made of a case where the diaphragm 80 is formed by using the metal surface 74 of the light blocking member 70. In this case, as illustrated in FIG. 9, the diaphragm 80 is provided between the light transmissive member 30 and the detector 130 (the light receiving portion 140). As mentioned above, if the diaphragm 80 is provided between the light transmissive member 30 and the detector 130, stray light can be effectively blocked by the diaphragm 80 on the optical path between a subject and the detector 130, and thus it is possible to effectively prevent a situation in which noise is superimposed on measured data due to the stray light. However, a method of disposing and forming the diaphragm 80 is not limited thereto and variously modified. For example, the diaphragm 80 may be provided between the light transmissive member 30 and a subject, or may be provided inside the light transmissive member 30.

Figure 11A:
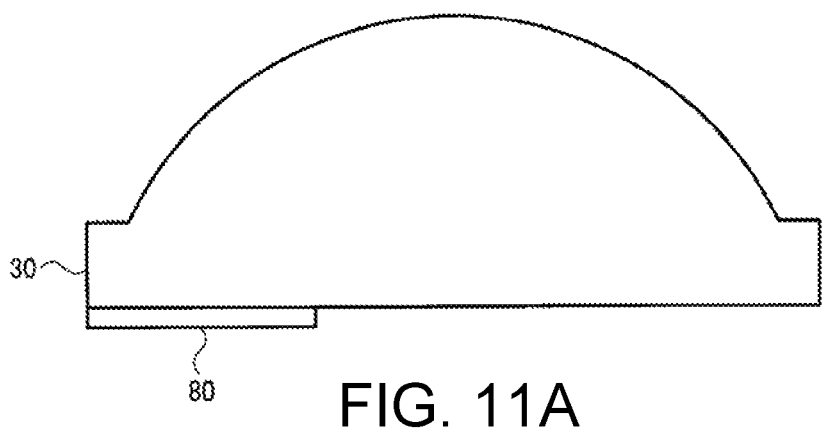
FIGS. 11(A) to 11(C) are diagrams illustrating other examples of positions where a diaphragm is disposed.

For example, in FIG. 11(A), the diaphragm 80 is provided between the light transmissive member 30 and the detector 130 (the light receiving portion 140), but the diaphragm 80 is disposed and is formed so as to adhere tightly to the light transmissive member 30. In addition, in FIG. 11(B), the diaphragm 80 is disposed and is formed inside the light transmissive member 30 (inside the material). Further, in FIG. 11(C), the diaphragm 80 is disposed and is formed between a subject and the light transmissive member 30. As mentioned above, various aspects may be employed regarding a method of disposing and forming the diaphragm 80.

Figure 11B:
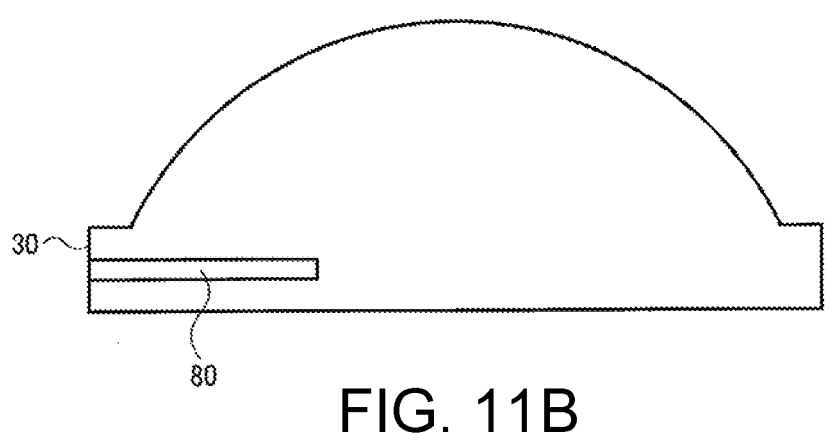
Figure 11C:
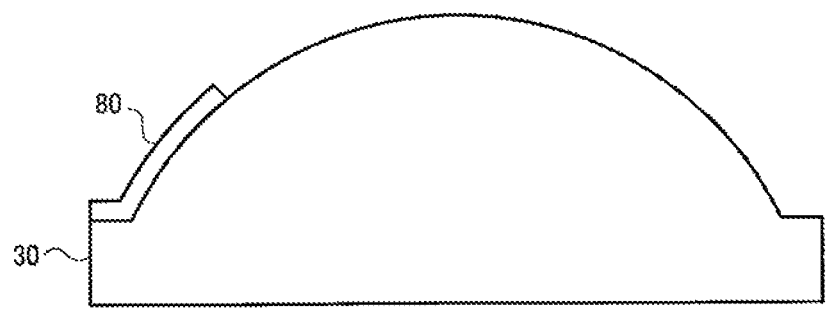

In addition, a method of forming the diaphragm 80 is not limited to the method of using the metal surface 74 having undergone the sheet metal processing as illustrated in FIG. 1, and may employ various methods. For example, in a case where the diaphragm 80 is formed so as to adhere tightly to the light transmissive member 30 as illustrated in FIGS. 11(A) and 11(C), the diaphragm 80 may be formed by using a method such as painting, depositing, or printing. Alternatively, in a case where the diaphragm 80 is disposed inside the light transmissive member 30 as illustrated in FIG. 11(B), the diaphragm 80 may be formed by using a method such as insert molding.

5. Convex Portion of Light Transmissive Member

Figure 12A:
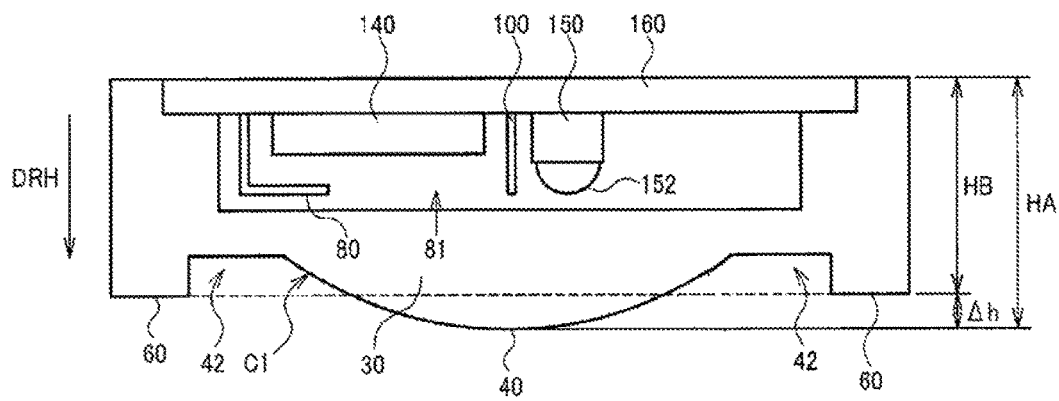
FIGS. 12(A) and 12(B) are diagrams illustrating a convex portion and a pressing restricting portion of the light transmissive member.

As illustrated in FIG. 12(A), in the present embodiment, the light transmissive member 30 includes the convex portion 40 which comes into contact with a subject and applies pressing to the subject during measurement of biological information of the subject.

In addition, the diaphragm 80 blocks light which has passed through a circumferential edge region of the convex portion 40 as indicated by C1. In the above-described way, it is possible to minimize deterioration or the like in reliability of measured data due to stray light at a location where a contact state is unstable as in C1.

In addition, in FIG. 12(A), the pressing restricting portion 60 is provided. The pressing restricting portion 60 is provided so as to surround the convex portion 40 on the casing surface (the surface on the subject side) of the biological information detection device and restricts pressing which is applied to the subject by the convex portion 40. The pressing restricting portion 60, in FIG. 8 and FIG. 9, includes the pressing restricting surface which extends from the position of the convex portion 40 in the second direction DR2 side (the direction side from the hand toward the lower arm). Specifically, the pressing restricting portion 60 is formed of the bank-shaped portion formed at the cover member 20.

In this case, for example, when a height of the convex portion 40 in the direction DRH perpendicular to the casing surface of the biological information detection device is indicated by HA (for example, a height of the top of the curved shape of the convex portion 40), a height of the pressing restricting portion 60 is indicated by HB (for example, a height at the highest location), and a value obtained by subtracting the height HB from the height HA (a difference between the height HA and the height HB) is indicated by $\Delta h$, a relationship of $\Delta h = HA-HB > 0$. For example, the convex portion 40 protrudes from the pressing restricting surface of the pressing restricting portion 60 toward the subject so as to satisfy $\Delta h > 0$. In other words, the convex portion 40 protrudes further toward the subject side by $\Delta h$ than the pressing restricting surface of the pressing restricting portion 60.

As mentioned above, if the convex portion 40 which satisfies $\Delta h > 0$ is provided, for example, initial pressing for exceeding a vein vanishing point can be applied to the subject. In addition, if the pressing restricting portion 60 for restricting pressing which is applied to the subject by the convex portion 40 is provided, it is possible to minimize a pressing change in a usage range in which measurement of biological information is performed by the biological information detection device, and thus to reduce a noise component or the like. Here, the vein vanishing point is a point in which a signal caused by the vein, superimposed on a pulse wave signal vanishes or decreases to an extent of not influencing pulse wave measurement when a pressing force is gradually increased in a state in which the convex portion 40 is brought into contact with the subject.

Figure 12B:
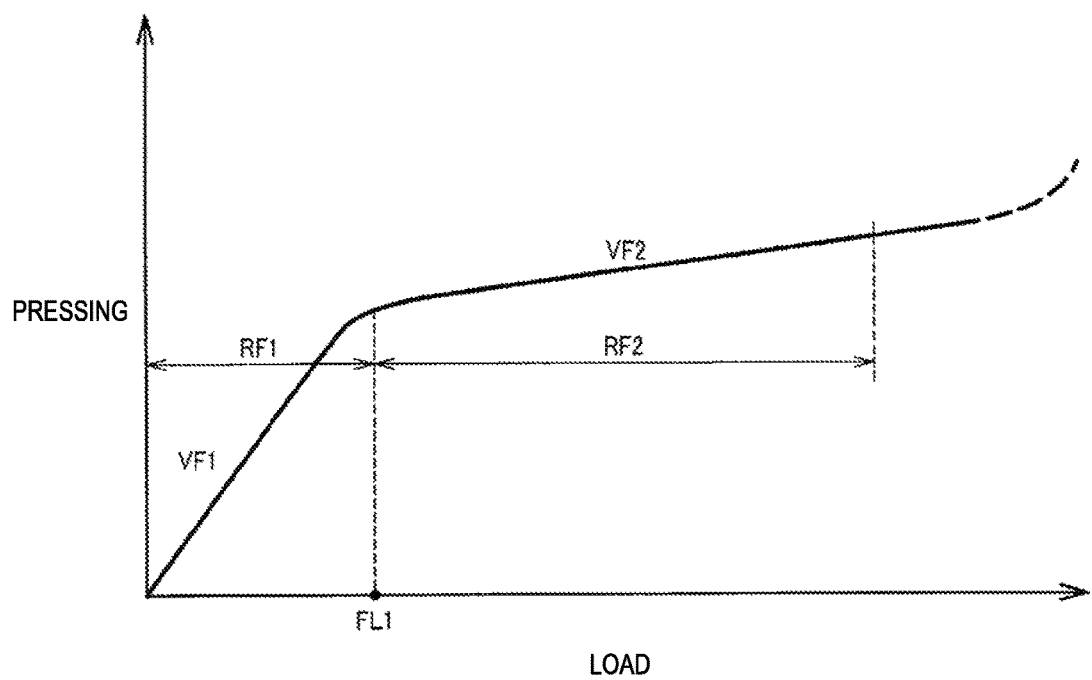

For example, in FIG. 12(B), a transverse axis expresses a load generated by the load mechanism (the mechanism constituted of the elastic member such as a spring or an extendable portion, or a band) described with reference to FIGS. 6(B) to 7(C), and a loxa expresses pressing (pressure applied to blood vessels) which is applied to the subject by the convex portion 40. In addition, an amount of changes in pressing of the convex portion 40 relative to a load applied by the load mechanism which generates pressing in the convex portion 40 is referred to as a pressing change amount. The pressing change amount corresponds to a slope of a pressing change characteristic relative to a load.

In this case, the pressing restricting portion 60 restricts pressing which is applied to a subject by the convex portion 40 so that a pressing change amount VF2 in a second load range RF2 in which a load caused by the load mechanism becomes greater than FL1 is reduced with respect to a pressing change amount VF1 in a first load range RF1 in which a load caused by the load mechanism becomes 0 to FL1. In other words, whereas the pressing change amount VF1 is increased in the first load range RF1 which is an initial pressing range, the pressing change amount VF2 is reduced in the second load range RF2 which is a usage range of the biological information detection device.

In other words, in the first load range RF1, the pressing change amount VF1 is increased so that the slope of the pressing change characteristic relative to the load is increased. The pressing with such a great slope of the change characteristic is realized by $\Delta h$ corresponding to a protruding extent of the convex portion 40. In other words, if the convex portion 40 satisfying $\Delta h > 0$ is provided, sufficient initial pressing which is necessary to exceed the vein vanishing point can be applied to a subject even in a case where a load caused by the load mechanism is small.

On the other hand, in the second load range RF2, the pressing change amount VF2 is reduced so that the slope of the pressing change characteristic relative to the load is reduced. The pressing with such a small slope of the change characteristic is realized by the pressing restricting portion 60 restricting pressing. In other words, if the pressing restricting portion 60 restricts pressing which is applied to a subject by the convex portion 40, a change in the pressing can be minimized even in a case where there is a change in the load in the usage range of the biological information detection device. Thus, it is possible to reduce a noise component.

As mentioned above, if optimized pressing (for example, about 16 kPa) is made to be applied to a subject, a signal component (M) of the pulse wave sensor can be increased, and a noise component (N) can be reduced. In addition, if a range of pressing used for measurement of a pulse wave is set to a range corresponding to the second load range RF2, pressing changes can be reduced to the minimum pressing changes (for example, about ±4 kPa), and thus a noise component can be reduced. Further, a noise component included in a pulse wave detection signal can be further reduced by reducing optical noise by using the diaphragm 80 or the light blocking wall 100.

Meanwhile, $\Delta h$ representing a protruding extent of the convex portion 40 is an important parameter which defines the optimum pressing. In other words, in order to apply pressing for exceeding the vein vanishing point at all times, protrusion is necessary to an extent, and a value of $\Delta h$ is required to be great. However, if a value of $\Delta h$ is excessive, there is a concern that this may cause a signal component of the pulse wave sensor to be reduced or a pressing change to be increased.

Therefore, the minimum $\Delta h$ is selected within a range in which a signal component of the pulse wave sensor can be sufficiently secured, that is, a range in which the optimum pressing can be applied. In other words, within a range in which the optimum pressing can be applied, as Δh becomes smaller, a noise component can be reduced to a lower level.

Specifically, a range of Δh is preferably 0.01 mm≤Δh≤0.5 mm, and is more preferably 0.05 mm≤Δh≤0.35 mm. For example, if Δh is set to about 0.25 mm, an MN ratio (SN ratio) can be made highest. In other words, if Δh is set to a small value, it is possible to minimize an increase in a noise component due to a pressing change or the like while applying the minimum pressing for exceeding the vein vanishing point to a subject, and also to increase an MN ratio indicating signal quality.

6. Entire Configuration of Biological Information Detection Device

Figure 13:
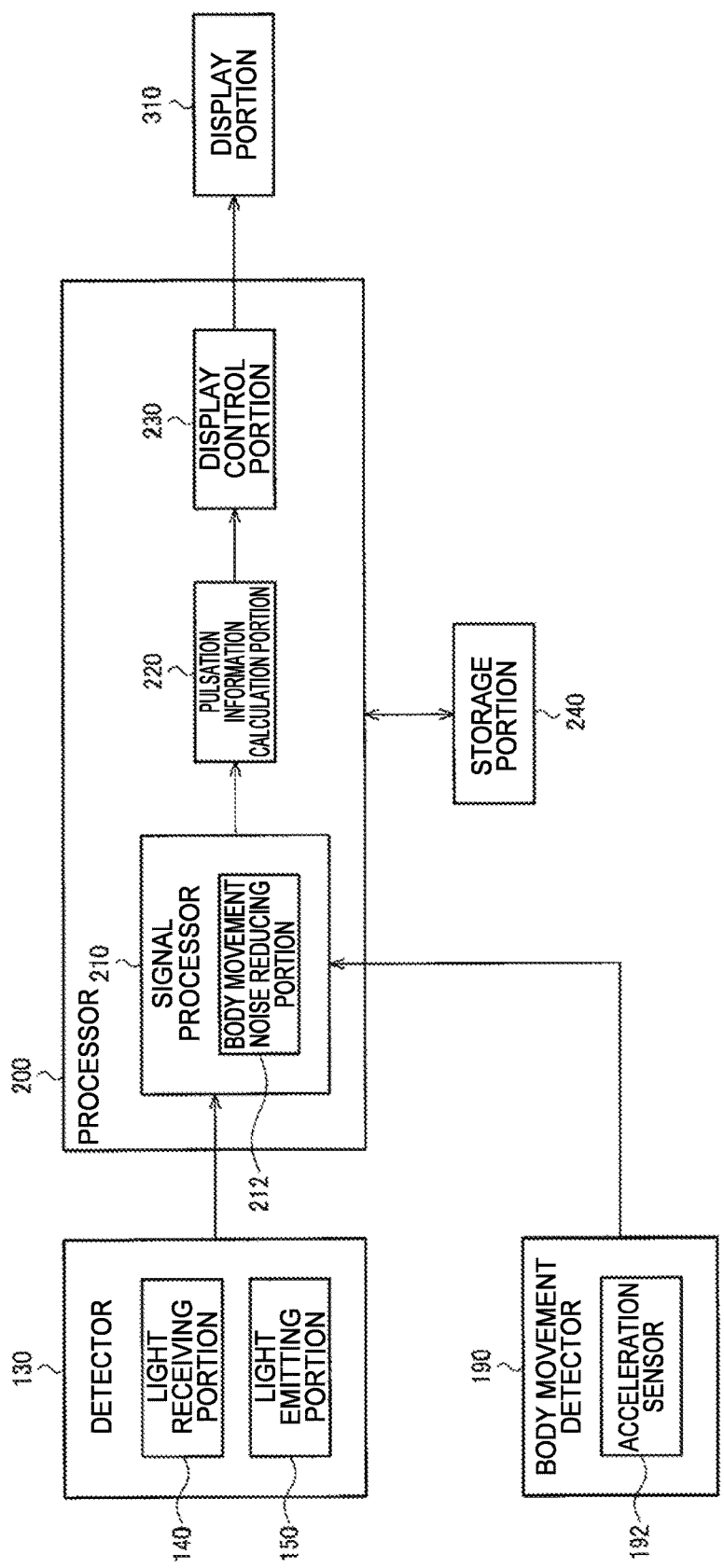
FIG. 13 is a functional block diagram illustrating an example of the entire configuration of the biological information detection device.

FIG. 13 is a functional block diagram illustrating an example of the entire configuration of the biological information detection device. The biological information detection device illustrated in FIG. 13 includes the detector 130, a body movement detector 190, a processor 200, a storage portion 240, and the display portion 310. In addition, the biological information detection device of the present embodiment is not limited to the configuration illustrated in FIG. 13, and may be variously modified by omitting some of the constituent elements or adding other constituent elements thereto.

The detector 130 detects biological information such as a pulse wave, and includes the light receiving portion 140 and the light emitting portion 150. A pulse wave sensor (photoelectric sensor) is implemented by the light receiving portion 140, the light emitting portion 150, and the like. The detector 130 outputs a signal detected by the pulse wave sensor as a pulse wave detection signal.

The body movement detector 190 outputs a body movement detection signal which is a signal which changes according to a body movement, on the basis of sensor information from various sensors. The body movement detector 190 includes, for example, an acceleration sensor 192 as a body movement sensor. In addition, the body movement detector 190 may include a pressure sensor or a gyro sensor as a body movement sensor.

The processor 200 performs various signal processes or control processes by using, for example, the storage portion 240 as a work area, and is implemented by a processor such as a CPU, or a logic circuit such as ASIC. The processor 200 includes a signal processor 210, a pulsation information calculation portion 220, and a display control portion 230.

The signal processor 210 performs various signal processes (including a filter process and the like), and performs signal processes on, for example, a pulse wave detection signal from the detector 130 or a body movement signal from the body movement detector 190. For example, the signal processor 210 includes a body movement noise reducing portion 212. The body movement noise reducing portion 212 performs a process of reducing (removing) a body movement noise which is noise caused by a body movement from the pulse wave detection signal on the basis of the body movement detection signal from the body movement detector 190. Specifically, a noise reduction process is performed by using, for example, an adaptive filter.

The pulsation information calculation portion 220 performs a pulsation information calculation process on the basis of a signal or the like from the signal processor 210. The pulsation information is, for example, information regarding a pulse rate. Specifically, the pulsation information calculation portion 220 performs a frequency analysis process such as FFT on a pulse wave detection signal having undergone a noise reduction process in the body movement noise reducing portion 212 so as to obtain a spectrum, and performs a process of setting a representative frequency in the obtained spectrum as a pulsation frequency. A value obtained by multiplying the obtained frequency by 60 is a pulse rate (heart rate) which is generally used. In addition, the pulsation information is not limited to a pulse rate itself, and may be various pieces of information (for example, a frequency or a cycle of heartbeats) indicating the pulse rate. Further, the pulsation information may be information indicating a pulsation state, and may be a value indicating a blood volume itself.

The display control portion 230 performs display control for displaying various pieces of information or images on the display portion 310. For example, as illustrated in FIG. 6(A), control is performed so that various pieces of information including pulsation information such as a pulse rate, and time information are displayed on the display portion 310. In addition, instead of the display portion 310, a notification device may be provided which performs output for stimulating a user's perception, such as light, sound or vibration. Such a notification device may include, for example, an LED, a buzzer, or a vibrator.

Although the present embodiment has been described in detail, it is easily understood by a person skilled in the art that various modifications may occur without substantially departing from the novel matters and effects of the invention. Therefore, such modification examples are all intended to be included in the scope of the invention. For example, in the specification or the drawings, a terminology which is described at least once along with another terminology which has a broader meaning or the same meaning may be replaced with another terminology in any location of the specification or the drawings. In addition, configurations and operations of the optical detection unit and the biological information detection device are not limited to those described in the present embodiment and may be variously modified.

The invention claimed is:

1. An optical detection unit comprising:
 a light emitting portion that emits light toward a target object;
 a light receiving portion that receives light from the target object; and
 a light blocking member between the light emitting portion and the light receiving portion,
 wherein the light blocking member is made of a metal,
 wherein the light blocking member is formed of a first metal wall, the first metal wall defining a first thickness, and wherein the first metal wall is between the light emitting portion and the light receiving portion,
 wherein the light blocking member is provided with a second metal wall and a third metal wall that are provided in a direction perpendicular to the first metal wall, the second metal wall defining a second thickness and the third metal wall defining a third thickness, and wherein the second metal wall and the third metal wall are spaced from each other a first distance,
 wherein the first metal wall defines a first length configured to cover ends of the second and third metal walls, and wherein the first length is greater than the second thickness, the third thickness, and the first distance combined; and
 wherein the first metal wall and the second metal wall are provided so as to be adjacent to each other via a first gap region, and the first metal wall and the third metal wall are provided so as to be adjacent to each other via a second gap region.

2. The optical detection unit according to claim 1, wherein the light blocking member further includes
a fourth metal wall that is provided in a direction intersecting the first metal wall and blocks light from being incident to the light receiving portion, and
wherein the fourth metal wall is provided with a diaphragm which restricts light from the target object on an optical path between the target object and the light receiving portion.

3. The optical detection unit according to claim 2, wherein the fourth metal wall couples to the first metal wall and defines an aperture.

4. The optical detection unit according to claim 3, wherein the aperture in the fourth metal wall is semi-circular.

5. The optical detection unit according to claim 3, comprising a fifth metal wall coupled to the fourth metal wall, wherein the first metal wall and the fifth metal wall couple to opposite sides of the fourth metal wall.

6. The optical detection unit according to claim 1, wherein a distance LD between the light emitting portion and the light receiving portion satisfies LD<3 mm.

7. The optical detection unit according to claim 6, wherein the distance LD satisfies 0.3 mm<LD<2.5 mm.

8. The optical detection unit according to claim 1, further comprising:
a board on which the light emitting portion, the light receiving portion, and the light blocking member are mounted,
wherein the light blocking member further includes
first and second projections that are engaged with holes of the board in order to fix the light blocking member to the board, and
wherein the first and second projections are provided at positions which are linearly asymmetric to each other with respect to a central line of the light blocking member.

9. A biological information detection device comprising the optical detection unit according to claim 1.

* * * * *